(12) United States Patent  
Chappell et al.

(10) Patent No.: US 10,597,665 B1  
(45) Date of Patent: Mar. 24, 2020

(54) METHOD AND SYSTEM FOR DITERPENE PRODUCTION PLATFORMS IN YEAST

(71) Applicant: University of Kentucky Research Foundation, Lexington, KY (US)

(72) Inventors: Joe Chappell, Lexington, KY (US); Xun Zhuang, Lexington, KY (US); Shuiqin Wu, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 14/092,286

(22) Filed: Nov. 27, 2013

Related U.S. Application Data

(60) Provisional application No. 61/730,412, filed on Nov. 27, 2012.

(51) Int. Cl.
  *C12N 15/81* (2006.01)
  *C12N 15/01* (2006.01)

(52) U.S. Cl.
  CPC ............. *C12N 15/81* (2013.01); *C12N 15/01* (2013.01)

(58) Field of Classification Search
  None
  See application file for complete search history.

(56) References Cited

U.S. PATENT DOCUMENTS

| | | | |
|---|---|---|---|
| 7,238,514 B2 * | 7/2007 | Matsuda | C12N 9/1085 435/193 |
| 2002/0040488 A1 * | 4/2002 | Chappell et al. | 800/278 |
| 2002/0094556 A1 | 7/2002 | Chappell et al. | |
| 2002/0094557 A1 | 7/2002 | Chappell et al. | |
| 2003/0087406 A1 | 5/2003 | Chappell et al. | |
| 2004/0053386 A1 | 3/2004 | Chappell et al. | |
| 2009/0053797 A1 * | 2/2009 | Shiba | C12P 23/00 435/254.21 |
| 2011/0039299 A1 | 2/2011 | Bailey et al. | |

OTHER PUBLICATIONS

Tarshis et al. 1994 (Crystal Structure of Recombinant Farnesyl Diphosphate Synthase at 2.6 A Resolution; Biochemistry 33:10871-10877).*
Fernandez et al. 2000 (Farnesyl Diphosphate Synthase: Altering the Catalytic Site to Select for Geranyl Diphosphate Activity; Biochemistry 39: 15316-15321).*
Genetic Nomenclature Guide. 1998. SGD (*Saccharomyces* Genome Database) http://genome-www.stanford.edu/Saccharomyces/.*
Takahashi et al. 2007 (Metabolic Engineering of Sesquiterpene Metabolism in Yeast; Biotechnology and Bioengineering; 97(1):170-181).*
Kayscek et al. 2015 (Yeast as a cell factory: current state and perspectives; Microbial Cell Factories 14:94). (Year: 2015).*
Zhuang et al. 2015 (Building Terpene Production Platforms in Yeast; Biotechnology and Bioengineering 112(9): 1854-1864; which is a post-filing by the inventors and appears to describe the claimed yeast). (Year: 2015).*
Vu, Shuiqin, et al., "Engineering Triterpene Metabolism in Tobacco", Planta, (2012).
Anderson M, Che P, Song J, Nikolau B, Wurtele E, 1998. 3-Methylcrotonyl-coenzyme A carboxylase is a component of the mitochondrial leucine catabolic pathway in plants. Plant physiology 118, 1127-38.
Anterola A, Shanle E, Perroud P-F, Quatrano R (2009) Production of taxa-4(5),11(12)-diene by transgenic Physcomitrella patens. Transgenic Research 18: 655-660.
Asadollahi MA, Maury J, Schalk M, Clark A, Nielsen J, 2010. Enhancement of Farnesyl Diphosphate Pool as Direct Precursor of Sesquiterpenes Through Metabolic Engineering of the Mevalonate Pathway in *Saccharomyces cerevisiae*. Biotechnology and bioengineering 106, 86-96.
Barkovich R, Liao JC, 2001. Metabolic engineering of isoprenoids. Metabolic engineering 3, 27-39.
Bhilwade HN, Tatewaki N, Nishida H, Konishi T, 2010. Squalene as Novel Food Factor. Current Pharmaceutical Biotechnology 11, 875-80.
Bitter GA, Egan KM (1984) Expression of Heterologous Genes in *Saccharomyces-cerevisiae* From Vectors Utilizing the Glyceraldehyde-3-Phosphate Dehydrogenase Gene Promoter Gene 32: 263-274.
Bourot S, Karst F (1995) Isolation and Characterization of the *Saccharomyces-cerevisiae* Sut1 Gene Involved in Sterol Uptake. Gene 165: 97-102.
Bouvier F, Rahier A, Camara B, 2005. Biogenesis, molecular regulation and function of plant isoprenoids. Progress in lipid research 44, 357-429.
Buchanan B, Gruissem W, Jones R, 2002. Biochemistry & Molecular Biology of Plants. John Wiley & Sons.
Burke YD, Stark MJ, Roach SL, Sen SE, Crowell PL, 1997. Inhibition of pancreatic cancer growth by the dietary isoprenoids farnesol and geraniol. Lipids 32, 151-6.
Cardenas C, Quesada AR, Medina MA (2011) Anti-Angiogenic and Anti-Inflammatory Properties of Kahweol, a Coffee Diterpene. Plos One 6.
Carrau FM, Medina K, Boido E, et al., 2005. De novo synthesis of monoterpenes by *Saccharomyces cerevisiae* wine yeasts. FEMS microbiology letters 243, 107-15.
Casida JE (2009) Pest Toxicology: The Primary Mechanisms of Pesticide Action. Chemical Research in Toxicology 22: 609-619.
DeJong JM, Liu YL, Bollon AP, Long RM, Jennewein S, Williams D, Croteau RB (2006) Genetic engineering of Taxol biosynthetic genes in *Saccharomyces cerevisiae*. Biotechnology and Bioengineering 93: 212¬924.
Engels B, Dahm P, Jennewein S (2008) Metabolic engineering of taxadiene biosynthesis in yeast as a first step towards Taxol (Paclitaxel) production. Metabolic Engineering 10: 201-206.

(Continued)

*Primary Examiner* — Mary Maille Lyons
(74) *Attorney, Agent, or Firm* — Stephen J. Weyer, Esq.; Stites & Harbison, PLLC

(57) ABSTRACT

A method is provided for modifying yeast to express mutant avian farnesyl disphospate synthase and the resulting modified yeast. The yeast advantageously includes additional mutants including but not limited to having ergosterol dependent growth and being erg-. The modified yeast are beneficial for the production of various terpenes including diterpenes.

16 Claims, 15 Drawing Sheets

Specification includes a Sequence Listing.

(56) References Cited

OTHER PUBLICATIONS

Farhi M, Marhevka E, Masci T, et al., 2011. Harnessing yeast subcellular compartments for the production of plant terpenoids. Metabolic engineering 13, 474-81.

Fernandez SMS, Kellogg BA, Poulter CD (2000) Farnesyl diphosphate synthase. Altering the catalytic site to select for geranyl diphosphate activity. Biochemistry 39: 15316-15321.

Fischer MJC, Meyer S, Claudel P, Bergdoll M, Karst F, 2011. Metabolic Engineering of Monoterpene Synthesis in Yeast. Biotechnology and Bioengineering 108, 1883-92.

Grassmann J (2005) Terpenoids as plant antioxidants. In G Litwack, ed, Plant Hormones, vol. 72, pp. 505-535.

Havaux M, Dall'Osto L, Cuine S, Giuliano G, Bassi R (2004) The effect of zeaxanthin as the only xanthophyll on the structure and function of the photosynthetic apparatus in *Arabidopsis thaliana*. Journal of Biological Chemistry 279: 13878-13888.

Hick AJ, Luszniak MC, Pickett JA, 1999. Volatile isoprenoids that control insect behaviour and development. Natural Product Reports 16, 39-54.

Huang Z-R, Lin Y-K, Fang J-Y, 2009. Biological and Pharmacological Activities of Squalene and Related Compounds: Potential Uses in Cosmetic Dermatology. Molecules 14, 540-54.

Janke C, Magiera MM, Rathfelder N, Taxis C, Reber S, Maekawa H, Moreno-Borchart A, Doenges G, Schwob E, Schiebel E, Knop M (2004) A versatile toolbox for PCR-based tagging of yeast genes: new fluorescent proteins, more markers and promoter substitution cassettes. Yeast 21: 947-962.

Kovacs K, Zhang L, Linforth RST, Whittaker B, Hayes CJ, Fray RG (2007) Redirection of carotenoid metabolism for the efficient production of taxadiene taxa-4(5),11(12)-diene in transgenic tomato fruit. Transgenic Research 16: 121-126.

Maertens JA (2004) History of the development of azole derivatives. Clinical Microbiology and Infection 10: 1-10.

Maimone TJ, Baran PS, 2007. Modern synthetic efforts toward biologically active terpenes. Nature chemical biology 3, 396-407.

Martin VJJ, Pitera DJ, Withers ST, Newman JD, Keasling JD, 2003. Engineering a mevalonate pathway in *Escherichia coli* for production of terpenoids. Nature Biotechnology 21, 796-802.

Mateus C, Avery SV (2000) Destabilized green fluorescent protein for monitoring dynamic changes in yeast gene expression with flow cytometry. Yeast 16: 1313-1323.

Maury J, Asadollahi MA, Moller K, Clark A, Nielsen J, 2005. Microbial isoprenoid production: an example of green chemistry through metabolic engineering. Advances in biochemical engineering/biotechnology 100, 19-51.

Mumberg D, Muller R, Funk M (1995) Yeast Vectors for the Controlled Expression of Heterologous Proteins in Different Genetic Backgrounds. Gene 156: 119-122.

Nicolaou KC, Yang Z, Liu JJ, Uenoll, Nantermet PG, Guy RK, Claiborne CF, Renaud J, Couladouros EA, Paulvannan K, Sorensen EJ (1994) Total Synthesis of Taxol. Nature 367: 630-634.

Ohnuma SI, Narita K, Nakazawa T, et al., 1996. A role of the amino acid residue located on the fifth position before the irst aspartate-rich motif of farnesyl diphosphate synthase on determination of the final product. The Journal of biological chemistry 271, 30748-54.

Roberts SC (2007) Production and engineering of terpenoids in plant cell culture. Nature Chemical Biology 3: 387-395.

Reddy LH, Couvreur P, 2009. Squalene: A natural triterpene for use in disease management and therapy. Advanced Drug Delivery Reviews 61, 1412-26.

Shianna KV, Dotson WD, Tope S, Parks LW (2001) Identification of a UPC2 homolog in *Saccharomyces cerevisiae* and its involvement in aerobic sterol uptake. Journal of Bacteriology 183: 830-834.

Takahashi S, Yeo Y, Greenhagen BT, McMullin T, Song L, Maurina-Brunker J, Rosson R, Noel JP, Chappell J (2007) Metabolic engineering of sesquiterpene metabolism in yeast. Biotechnology and Bioengineering 97: 170-181.

Tarshis LC, Proteau PJ, Kellogg BA, Sacchettini JC, Poulter CD (1996) Regulation of product chain length by isoprenyl diphosphate synthases. Proceedings of the National Academy of Sciences of the United States of America 93: 15018-15023.

Tohoyama H, Kadota H, Shiraishi E, Inouhe M, Joho M (2001) Induction for the expression of yeast metallothionein gene, CUP1, by cobalt. Microbios 104: 99-104.

Toyomasu T, Kawaide H, Ishizaki A, Shinoda S, Otsuka M, Mitsuhashi W, Sassa T (2000) Cloning of a full-length cDna encoding ent-kaurene synthase from *Gibberella fujikuroi*: Functional analysis of a bifunctional diterpene cyclase. Bioscience Biotechnology and Biochemistry 64: 660¬664.

Tu Y, 2011. The discovery of artemisinin (qinghaosu) and gifts from Chinese medicine. Nature Medicine 17, 1217-20.

Tudzynski B, Hedden P, Carrera E, Gaskin P (2001) The P450-4 gene of Gibberella fujikuroi encodes ent-kaurene oxidase in the gibberellin biosynthesis pathway. Applied and Environmental Microbiology 67: 3514¬3522.

Vogel BS, Wildung MR, Vogel G, Croteau R (1996) Abietadiene synthase from grand fir (Abies grandis)—cDNA isolation, characterization, and bacterial expression of a bifunctional diterpene cyclase involved in resin acid biosynthesis. Journal of Biological Chemistry 271: 23262-23268.

Wall ME, Wani MC (1995) Paclitaxel—From Discovery to Clinic. In Gicttoivdm Georg, ed, Taxane Anticancer Agents: Basic Science and Current Status, vol. 583, pp. 18-30.

Wu SQ, Schalk M, Clark A, Miles RB, Coates R, Chappell J (2006) Redirection of cytosolic or plastidic isoprenoid precursors elevates terpene production in plants. Nature Biotechnology 24: 1441-1447.

Yamaguchi S (2008) Gibberellin metabolism and its regulation. In Annual Review of Plant Biology, vol. 59, pp. 225-251.

Zhang DL, Jennings SM, Robinson GW, Poulter CD (1993) Yeast Squalene Synthase—Expression, Purification, and Characterization of Soluble Recombinant Enzyme. Archives of Biochemistry and Biophysics 304: 133-143.

Zhou YJ, Gao W, Rong Q, et al., 2012. Modular pathway engineering of diterpenoid synthases and the mevalonic acid pathway for miltiradiene production. Journal of the American Chemical Society 134, 3234-41.

Porto TS, Rangel R, Furtado N, de Carvalho TC, Martins CHG, Veneziani RCS, Da Costa FB, Vinholis AHC, Cunha WR, Heleno VCG, Ambrosio SR (2009) Pimarane-type Diterpenes: Antimicrobial Activity against Oral Pathogens. Molecules 14: 191-199.

\* cited by examiner

METHOD AND SYSTEM FOR DITERPENE PRODUCTION PLATFORMS IN YEAST

CROSS-REFERENCE TO RELATED APPLICATION

This application claims the benefit of U.S. provisional patent application Ser. No. 61/730,412, filed Nov. 27, 2012, and co-pending application filed Nov. 27, 2013, both herein incorporated by reference.

FIELD OF THE INVENTION

The presently-disclosed subject matter relates to methods for producing or generating modified yeast, and the resulting yeast, and in particular, yeast that can be used for various aspects of terpene production. For example, the subject matter relates to methods and systems for building terpene production platforms in yeast to express mutant avian farnesyl disphospate synthase. These platforms or cell lines can be further modified, e.g. genetically engineered to produce specific enzymes and/or terpenes, namely diterpenes.

BACKGROUND OF THE INVENTION

Plants, microorganisms and animals produce a large variety of organic chemical compounds, some of which are used universally for growth and metabolism and others seem to play specialized roles in the life cycle of the organism (Maimone & Baran, 2007). As such, two large classes of natural products are widely recognized. Primary metabolites are those essential for live in all eukaryotic organisms, while specialized metabolites appear to give species specific advantages for occupying distinct environmental niches. The distinctive role specialized metabolites play in an organisms natural history, for example how these metabolites provide protection against microbial challenge, have also not escape attention for their possible utility in a wide range of applications. For example, many of the currently used drugs are derived or inspired from plant-derived specialized chemicals and are commonly referred to as Natural Products (Buchanan et al., 2002). Capturing the chemical and structural diversity of Natural Products has recently been identified as a major objective within the scientific community in large part because of the wide array of applications Natural Products can have and the resulting economical implications.

Terpenes and terpenoids are a large and diverse family of Natural Products with more than 55,000 having been identified (Maimone & Baran, 2007). However, based on the biosynthetic mechanisms responsible for terpenes, chemists have predicted that only a small fraction of all the possible terpene compounds have been discovered (Bouvier et al., 2005). Terpenes are derived from the five carbon isoprene unit with different combinations of the isoprene units generating different classes of the terpene products. The classification and biosynthesis of terpenoids are based on the number of five-carbon units they contain as illustrated in FIG. 1. Monoterpenes (consisting of 10 carbons), sesquiterpenes (15 carbon derivatives), and diterpenes (20 carbon derivatives), arise from the corresponding intermediates geranyl diphosphate (GPP), farnesyl diphosphate (FPP), and geranylgeranyl diphosphate (GGPP). These intermediates in turn arise by the sequential head to tail condensation of C5 units. Higher order terpenes like triterpene (30 carbons) are formed from two farnesyl units condensed head-to-head. Likewise, tetraterpenes (40 carbons) are formed from two geranylgeranyl units condensed head-to-head.

Monoterpenes are well known as the volatile essence of flowers and plants and such mixtures can account for up to 5% of plant dry weight (Buchanan et al., 2002). Menthol and camphor are common monoterpenes found in diverse plant families and whose structural complexity in terms of stereo- and regio-chemistry are emphasized in FIG. 2. Besides providing pleasing fragrances, monoterpenes have been shown to function as signal molecules in defense mechanisms against pathogens (Hick et al., 1999). Hence, monoterpenes have the commercial value as flavors, fragrances, essential oils, and as anticancer and antimicrobial drugs (Burke et al., 1997). Sesquiterpenes (C15) are also found in essential oils, and many sesquiterpenes possess antibiotic activities, prompting suggestions that they are produced by plants as a defense mechanism. Diterpenes (C20) include gibberellins (plant hormones), vitamin A, as well as pharmaceutical important metabolites such as taxol, an exceptional anticancer regent (Barkovich & Liao, 2001). Triterpenes (C30) include the brassinosteroids, phytosterols important for lipid membrane composition, and components of surface waxes, such as oleanolic aid of grapes. Squalene, the major content of shark liver oil, is a linear triterpene and common ingredient in cosmetic products (Buchanan et al., 2002), has special utility as a lubricant for high performance machinery, and is a common adjuvant in many pharmaceutical formulations (Bhilwade et al., 2010, Huang et al., 2009, Reddy & Couvreur, 2009). Tetraterpenes (C40) include carotenoid accessory pigments, like lycopene, the monocyclic gamma-carotene, and the bicyclic alpha- and beta-carotenes, which perform essential for the light reactions of photosynthesis. Longer chain terpenes, so-called polyterpenes, contain more than 8 isoprene units and include examples like ubiquinone and rubber (Buchanan et al., 2002).

There are two pathways for terpene biosynthesis in plant cells. One is the mevalonate pathway pathway (MVA) which is well established and discovered in the 1960s (Bouvier et al., 2005). The other is the mevalonate independent pathway, or more properly referred to as the methylerythritol-phosphate pathway (MEP), which was more recently discovered (Bouvier et al., 2005). The MEP pathway was first discovered in prokaryote cells, and then confirmed to exist in plant cells (Barkovich & Liao, 2001). Interestingly, plants utilize these two pathways to meet different terpene biosynthetic needs. Sesquiterpenes, sterols, triterpenes and oligoterpenes (side chain of dolichols) are synthesized in the cytosol via the MVA pathway, while monoterpenes, diterpenes, teraterpenes, and polyterpenoids are synthesized in chloroplasts via the MEP pathway using pyruvate and glyceraldehydes-3-phosphate as the primary precursors (FIG. 2).

The principal product of the mevalonate pathway is sterols, for example cholesterol in animal cells, stigmasterol and campesterol in plant cells, and ergosterol in fungi, which all play essential roles in establishing the structural integrity of membranes, establishing permeability and fluidity, and also serving as signal compounds in cellular communication (Buchanan et al., 2002). In *Saccharomyces cerevisiae*, only the mevalonate pathway is known to operate and no components of the MEP pathway have been found (Maury et al., 2005). FIG. 3 shows the intermediates and the related genes involved in the yeast mevalonate pathway (Maury et al., 2005). Two molecules of acetyl-CoA are condensed by acetoacetyl-CoA thiolase, which is encoded by ERG10, to synthesize acetoacetyl-CoA. A second condensation reaction between acetoacetyl-CoA and acetyl-CoA is then catalyzed by HMG-CoA synthase encoded by ERG13 to yield 3-hydroxy-3methyglutaryl-CoA (HMG-CoA).

TABLE 1

Biological activities and commercial applications of typical terpenoids

| Class | Biologic activities | Commercial applications | Examples |
|---|---|---|---|
| Monoterpenoids | Signal molecules and used as defense mechanisms against pathogens | Flavors, fragrances, cleaning products, anticancer, antibacterial, antioxidant, essential oil, bionief | Limonence, menthol, camphor, linalool |
| Sesquiterpenoids | Antibiotic, antitumor, antiviral, immunosuppressive, and hormonal activities, defensive agents or pheromones | Flavors, fragrances, pharmaceuticals (antibacterial, antifungal), insecticides, biofuels | Nootkatone, artemisinin, patchoulol, nerolidol, farnesol, capsidol, farnesene, bisabolene |
| Diterpenoids | Hormonal activities, growth regulator, antitumor, antimicrobial and anti-inflammatory properties | Anticancer agents, feedstock for industrial chemical applications | Gibberellins, phytol, taxot, kaurerte, abietadiene, kaurenoic acid, abictic acid |
| Triterpenoids | Membrane component, steroid hormones | Biologic markers, biofuel, skin moisturizers in cosmetics, immunologic adjuvant in vaccines. | Sterols, hopanoids, squalene, botryococcene. |
| Tetraterpenoids | Antioxidants, photosynthetic components, pigments, and nutritional elements (vitamins) | Food additives, colorants, antioxidants | Lycopene, beta-carotene |

HMG-CoA is reduced by HMG-CoA reductase to yield mevalonate. This reaction is catalyzed by HMG-CoA reductase, which is encoded by 2 separate loci in yeast. Both loci appear to compensate for a knockout loss of the other gene. The C5 position of mevalonate is phosphorylated by mevalonate kinase, encoded by ERG12. Then a second kinase, phosphomevalonate kinase, encoded by ERGS, catalyzes the successive phosphorylation to yield diphosphomevalonate. In the next step the diphosphomevalonate is converted into IPP (isopentenyl diphosphate) by mevalonate diphosphate decarboxylase, encoded by ERG19. IPP isomerase, encoded by IDI1 converts IPP into DMAPP (dimethylallyl diphosphate). The condensation of the C5 building blocks of IPP and DMAPP into FPP is catalyzed by FPP synthase, which is encoded by ERG20. FPP can then be used as substrate for sterol and other isoprenoid biosynthetic needs.

Recent studies have discovered that FPP is also available in yeast mitochondria, as evidenced by increasing novel sesquiterpene production three-times by targeting a sesquiterpene synthase to the mitochondria compartment compared with targeting this same enzyme to the cytosol (Farhi et al., 2011). The origin of FPP in mitochondria could be the IPP and DMAPP arising in cytosol being imported and converted in the mitochondria to FPP. Alternatively, a hypothetical leucine metabolism model for the formation of terpene in *S. cerevisiae* is also a possibility. The leucine catabolism pathway (MCC pathway) is known to occur in the mitochondria of other eukaryotic mammal and plant cells (Anderson et al., 1998), in mitochondria leucine metabolite to form 3-Hydroxy-3-methylglutaryl-CoA, which can be catalyzed by HMGR to produce mevalonic acid, and then produce IPP and DMAPP through MVA pathway as shown in FIG. 4 (Carrau et al., 2005). Interestingly, a yeast line engineered with a chimeric diterpene synthase targeted to the cytoplasm along with prenyltransferases streamlined for GGPP biosynthesis, yielded 2-3 times more diterpene when the expression vector also provided a leu2 auxotrophic selection marker gene. The interpretation provided by the authors was that the extra leucine produced by the auxotrophic selection marker gene provided another source for IPP via the leucine catabolic pathway (FIG. 4). (Zhou et al., 2012).

Prenyltransferases generate allylic diphosphate esters GPP, FPP, and GGPP. These compounds can undergo a variety of reactions, which include cyclization reactions catalyzed by terpene synthases, yielding diverse terpenes based on regio- and stereo-chemical constraints built into the reactions. Prenyltransferases and terpene syntahases utilize electrophilic reaction mechanisms to mediate the catalytic reactions (Ohnuma et al., 1996) and typically share a conserved aspartate-rich DDXXD motif thought important for the initial substrate binding and metal-dependent ionization step leading to the first reaction carbocation intermediates. In the prenyltranferase reactions, the allylic diphosphate ester can be ionized to form a carbocation, then condensed with a second IPP in another round of elongation.

Terpenes are a very large class of structurally diverse compounds made by organisms in all kingdoms of life. The terpenes from plants are perhaps the most extensively described as evident by well over 100,000 different terpenes reported in the literature (Buckingham, 2003). Terpenes are also widely recognized for their diverse utility and applications. For example, taxol, a diterpene widely recognized for its application as a chemotherapeutic agent, was first isolated from the bark and needles of several *Taxus* plant species (Wall and Wani, 1995). Likewise, Artemisinin, a sesquiterpene isolated from the plant *Artemisia annua*, has been developed as a key pharmacological agent for the control of malaria (Tu, 2011). Patchouli, another sesquiterpene, is a popular aromatic found in colognes, perfumes and many other household cleaning products (Wu et al., 2006). Menthol is a monoterpene obtained from mint family plants and is a popular ingredient in many foods and consumer products (Bedoukian, 1983). Triterpenes such as squalene, obtained from various plant sources and the livers of deep sea sharks, have utility as a nutraceutical product, is used extensively in many types of cosmetics, has special utility as a lubricant for high performance machinery, and is a common adjuvant in many pharmaceutical formulations (Huang et al., 2009; Reddy and Couvreur, 2009; Bhilwade et al., 2010).

Terpenes are, however, generally made by plants and microbes in small amounts and components of complex mixtures that vary with growth and environmental conditions, making it difficult to reproducibly obtain large amounts of any one terpene constituent (Wu et al., 2006). Chemical synthesis of terpenes is often costly and inefficient (Nicolaou et al., 1994). Chemical synthesis also suffers from generating enantiomeric mixtures, which adds other complications if one particular stereochemical form of a terpene is desired. Given such difficulties, there are many on-going efforts to create robust, reliable and efficient biological systems for the production of distinct classes of terpenes, and more so for the generation of stereochemically pure forms of terpenes (Martin et al., 2003; Wu et al., 2006;

Takahashi et al., 2007; Asadollahi et al., 2008; Kirby et al., 2008; Seki et al., 2008; Keasling, 2009; Asadollahi et al., 2010; Fischer et al., 2011). The current invention disclosure describes the generation of yeast lines that we claim have utility for the production of diverse classes of terpenes including monoterpenes, sesquiterpenes, diterpenes and triterpenes.

Diterpenes are a class of compounds within the much larger terpene family of molecules (FIG. 4). Terpenes, in general, are built upon a 5 carbon repeating unit giving rise to classes of compounds having 10 (monoterpenes), 15 (sesquiterpenes), 20 (diterpenes), and more carbons. The current disclosure pertains to diterpenes, which are known to have diverse biological and practical applications. In plants, specific diterpenes serve as hormones or growth regulators (i.e. gibberellic acid derivatives) (Yamaguchi, 2008) while others serve as accessory photo-pigments funneling energy from light capture to the light reactions of photosynthesis (Havaux et al., 2004). Other diterpenes provide protection against oxidative radicals (Grassmann, 2005). The antioxidant activity of diterpenes has also led to their use in human nutraceuticals and medical applications (Cardenas et al., 2011). Perhaps the most widely recognized diterpene is taxol, used very successfully and extensively for the treatment of a variety of cancers (Wall and Wani, 1995). Specific diterpenes have also found use in the control of dental caries providing antimicrobial activities (Porto et al., 2009). Other diterpenes have found utility in manufacturing purposes, such as in the production of tackifers (U.S. Pat. No. 7,655, 739), herein incorporated by reference.

Diterpenes are traditionally obtained from plant sources. However, they are often found in only small amounts and as components of complex mixtures that vary with growth and environmental conditions, making it difficult to obtain large amounts of any one diterpene constituent (Wu et al., 2006). Chemical synthesis of diterpenes is often costly and inefficient (Nicolaou et al., 1994). Chemical synthesis also suffers from generating enantiomeric mixtures, which adds other complications if one particular stereochemical form of a terpene is desired. Given such difficulties, there are many on-going efforts to create robust, reliable and efficient biological systems for the production of distinct diterpenes, and more so for the generation of stereochemically pure forms of diterpenes (DeJong et al., 2006; Kovacs et al., 2007; Roberts, 2007; Engels et al., 2008; Anterola et al., 2009). The current invention disclosure describes the generation of yeast lines that we claim have utility for the production of diverse and high-value diterpenes.

SUMMARY OF THE INVENTION

The presently disclosed subject matter relates to methods for producing modified yeast cell lines to produce "platforms" in yeast and the resulting modified yeast or platforms. The production platforms can be further modified to produce specific terpenes such as diterpenes. Advantageously, the method includes modifying yeast to express avian farnesyl disphospate synthase and preferably mutant avian farnesyl disphospate synthase. The modification advantageously is provided by an expression vector encoding mutant avian farnesyl disphospate synthase. The expression vector can be inserted into wildtype yeast including but not limited to Candida albicans (C. albicans) and Saccharomyces cerevisiae (S. cerevisiae). These can be ergosterol (hereinafter "erg") erg- or erg+ and/or have sterol uptake enhancement (hereinafter "SUE") SUE+ or SUE–. Especially advantageous yeast platforms are both erg- and SUE+.

The mutant avian farnesyl disphospate synthase (mtFPS) converts dimethylallyl diphosphate (DMAPP) and isopentenyl diphosphate (IPP) to teganylgeranyldiphosphate (GGPP) and from GGPP to various desired diterpenes.

The present invention, in one form, relates to genetically modified yeast which expresses mtFPS. The yeast may be erg+ or erg- and/or SUE+ or SUE–.

The present invention, in another form thereof relates to a method for producing a genetically modified yeast comprising inserting an expression vector into a yeast cell wherein the expression vector expresses a gene for mtFPS.

The present invention, in another form thereof relates to a method for generating terpene produced yeast cell lines. The method includes combining yeast with a chemical mutagenesis agent to induce mutations in the yeast to generate chemically modified yeast. The chemically modified yeast are selected which grow in the presence of nysatin, squalestatin, and cholesterol followed by selecting for ergosterol dependent growth. The ergosterol dependent growth yeast are subjected to an erg9 knockout mutation to thereby produce ergosterol dependent growthlerg9 knockout mutation yeast cell lines. An expression vector is inserted into the ergosterol dependent growthlerg9 knockout mutation yeast cells wherein the expression vector expresses a gene for mtFPS.

DETAILED DESCRIPTION

The present method and modified yeast will now be described with reference to the figures and exemplary experiments, examples and methods. The figures, experiments and examples are merely to provide a more thorough understanding of the present method and modified yeast. However, other methods and generated yeast can be envisioned consistent with the scope and spirit of this disclosure.

Figure 1:
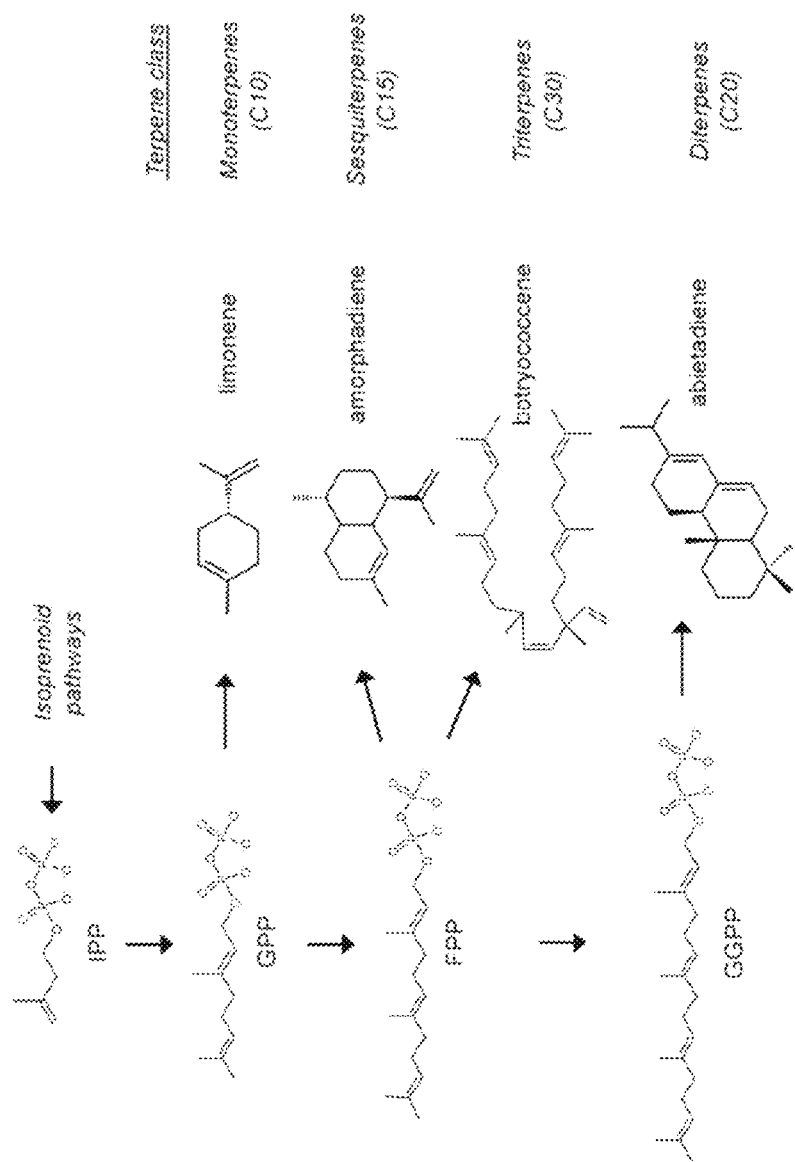
FIG. 1 shows biosynthesis of terpenes from natural sources, often in mixtures, produced by wild type yeast.
Figure 2:
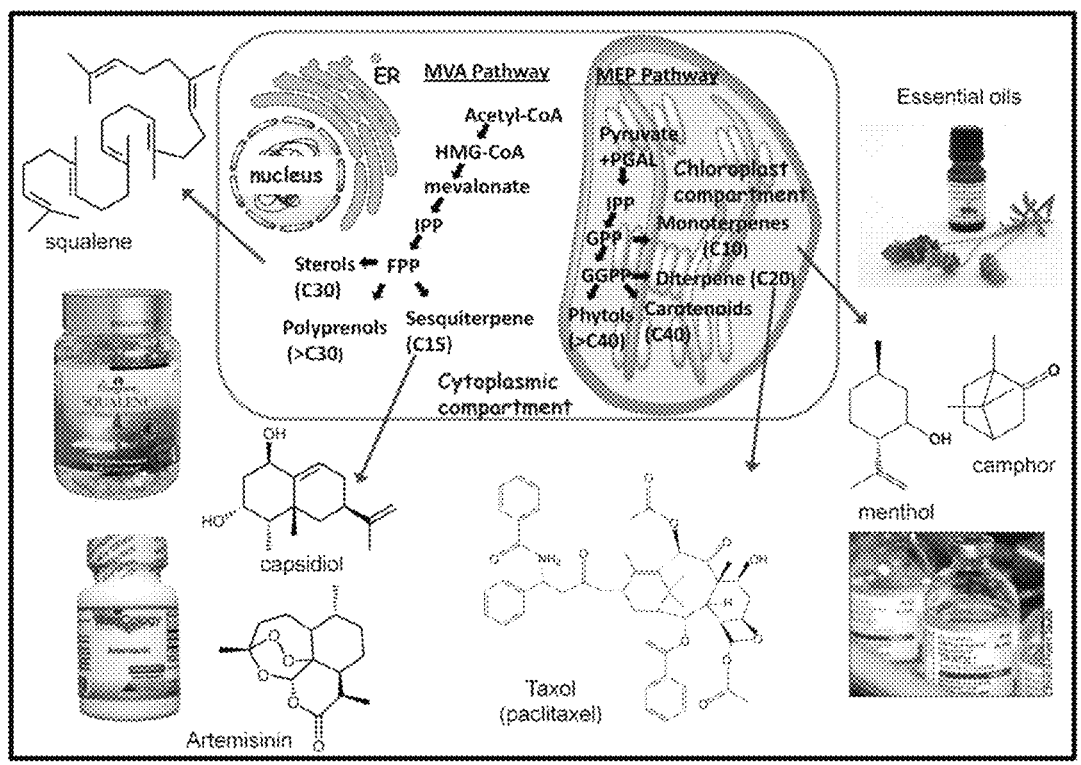
FIG. 2 is schematic outline of two terpene biosynthetic pathways that operate in plants (the MVA and MEP pathways), their intracellular locations, and examples of the chemical compounds derived from each.
Figure 3:
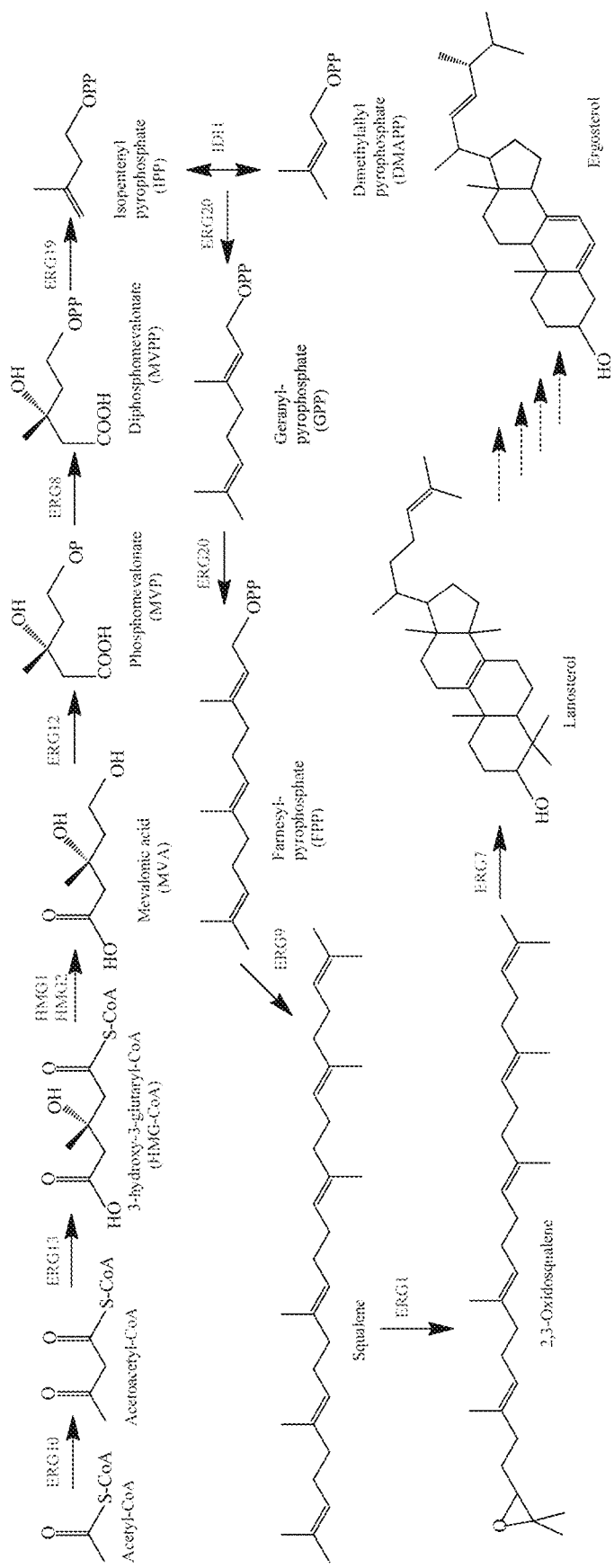
FIG. 3 illustrates mevalonate pathway in erogsterol biosynthesis in yeast (S. cerevisiae).
Figure 4:
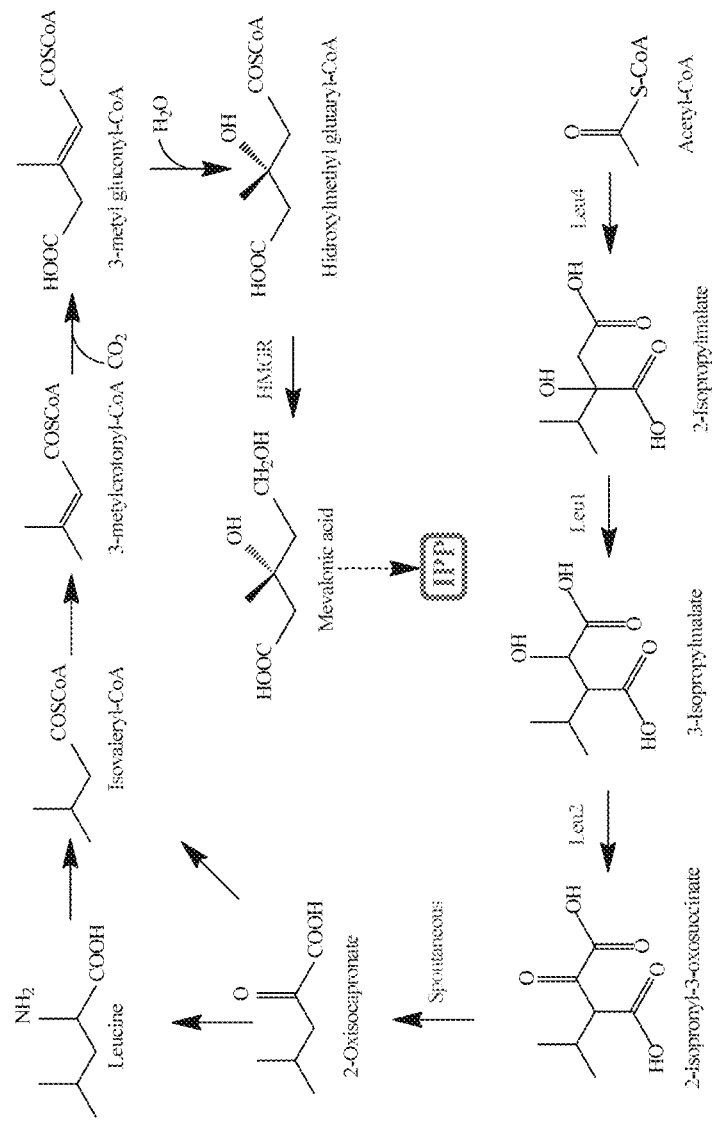
FIG. 4 is a schematic representing compounds of various terpenoid classes and prenyl diphosphates derived.
Figure 5:
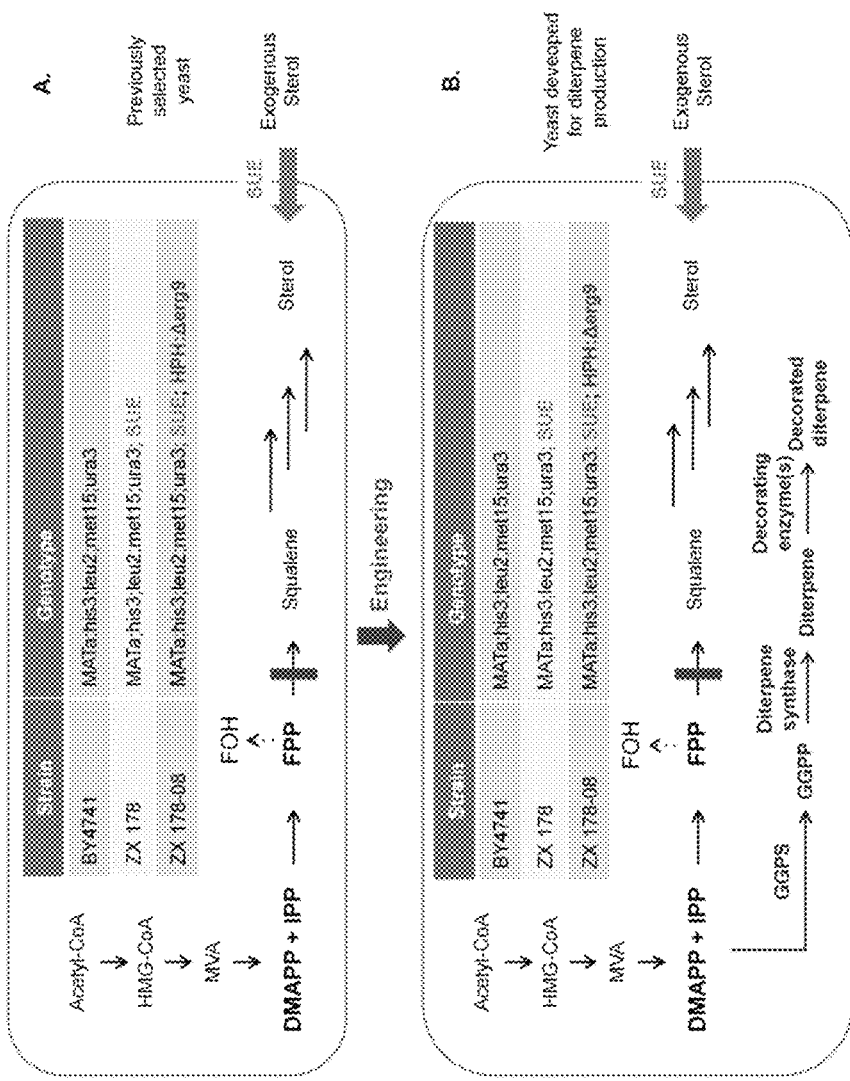
FIG. 5 is a schematic showing one strategy for developing a yeast line suitable for engineering diterpene chemicals in accordance with the present invention.

FIG. 5 outlines one approach used to generate yeast lines that provides for robust biosynthesis of precursors that can be utilized for the production of many different classes of terpenes. The schematic diagram in FIG. 5 shows an overall approach used for generating a yeast cell line that have a dispensable sterol biosynthetic pathway (FIG. 5, upper panel A), which provide opportunities for diverting intermediaries (DMAPP, IPP and FPP) from the mevalonate (MVA) pathway for the biosynthesis of diterpene compounds (FIG. 5, lower panel B).

The strategy takes advantage of the native mevalonate (MVA) pathway that operates normally in yeast for the biosynthesis of ergosterol, the dominant sterol found in yeast. Ergosterol is the main product of the yeast mevalonate pathway, is an important membrane component, and is essential for yeast growth. If the ergosterol biosynthetic pathway is blocked or inhibited, yeast die. In fact, this is the basis for many pharmacological drugs to control fungal infections in man (Maertens, 2004) and agricultural chemicals to control fungal infection in plants (Casida, 2009). To further complicate matters, wild type yeast can take up exogenously supplied sterol from their environment only under anaerobic conditions.

In order to be able to efficiently channel terpene biosynthetic intermediates from the ergosterol biosynthetic pathway (FIG. 5, panel A), a SUE (sterol uptake enhancement) mutation supporting the aerobic uptake and utilization of exogenous sterol was first created (Bourot and Karst, 1995; Shianna et al., 2001). A SUE mutation is thus a yeast line that can meet all its sterol needs by an exogenous source of sterol, and therefore making the endogenous ergosterol biosynthetic pathway dispensable (Bourot and Karst). The Bourot and Karst SUE mutation was then complemented by the introduction of a knockout mutation in the ERG9 gene (squalene synthase) (Zhang et al., 1993), resulting in a yeast line where the MVA pathway was still operational up to the biosynthesis of FPP and hence, intermediates in the pathway (DMAPP, IPP and FPP) could be diverted to the biosynthesis of other non-essential terpene components.

This technique diverts isoprenoid pathway intermediates to the biosynthesis of diterpenes, to provide high yielding conditions for the production of diterpene hydrocarbons and decorating the diterpene scaffolds to generate additional high-valued chemical entities.

Steps in the Development of High Level Diterpene Accumulation in Yeast

I. Co-Expression of a Mutant Prenyltransferase

Figure 6:
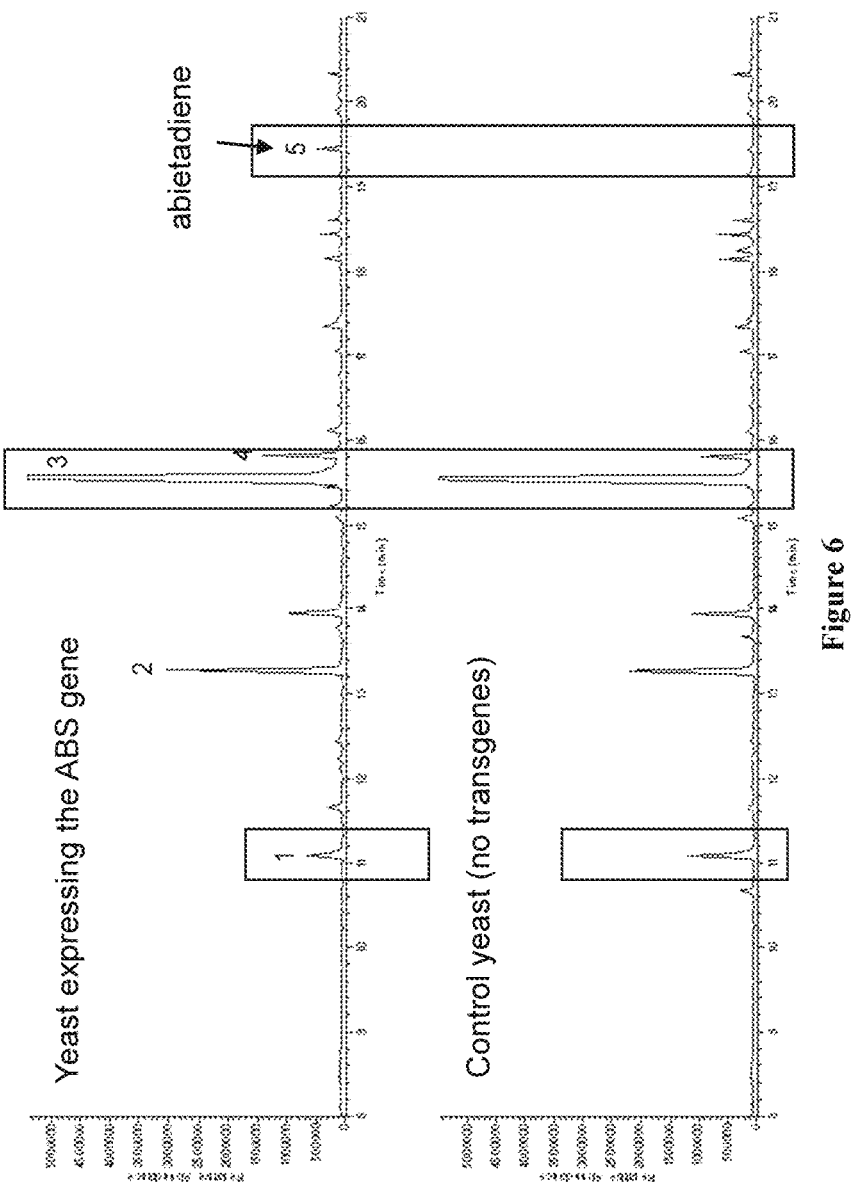
FIG. 6 is a graph showing a comparison of terpene chemical profiles in yeast over-expressing the abietadiene synthase (ABS) gene versus control yeast not harboring the ABS gene.
Figure 7:
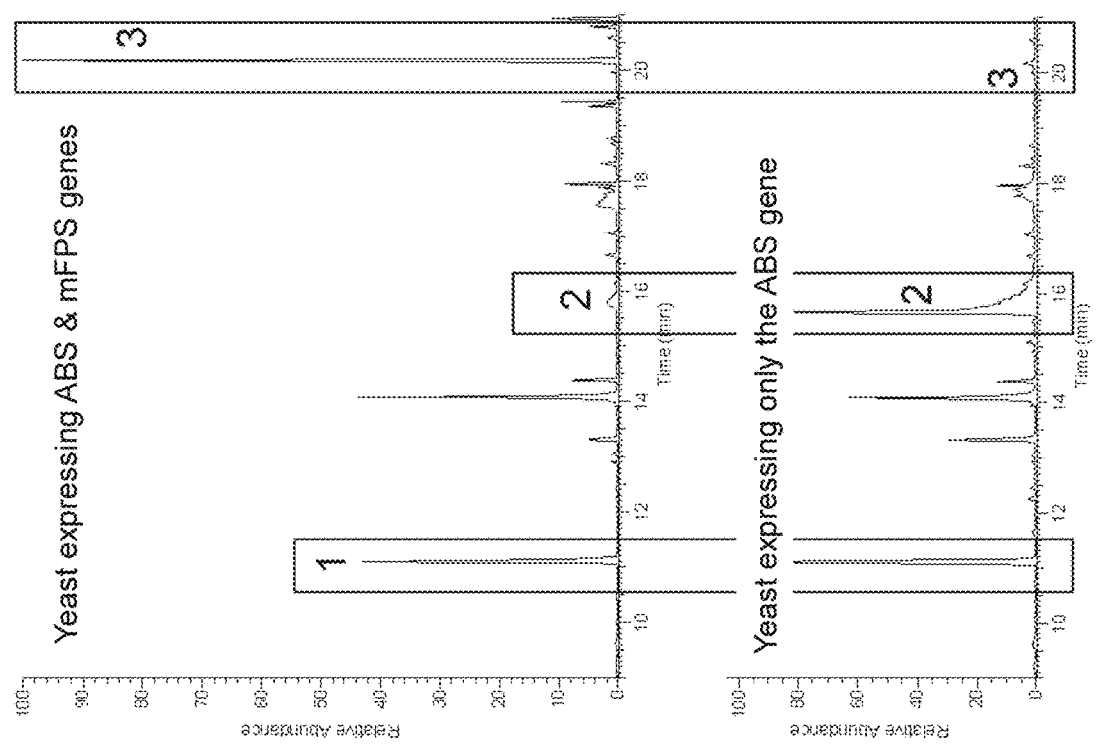
FIG. 7 is a graph showing a comparison of terpene chemical profiles from yeast co-expressing an alternative GGPP synthase (mFPS F112A) with abietadiene synthase versus only over-expressing the abietadiene synthase.

Specific efforts and conditions were necessary to generate yeast lines expressing high-level diterpene accumulation. The first was based on the observation that yeast engineered with a diterpene synthase, like abietadiene synthase, ABS (Vogel et al., 1996) tend to accumulate only marginal amounts of the desired diterpene product (FIG. 6). However, when expression of the ABS gene is coupled with the co-expression of a mutant avian farnesyl diphosphate synthase (mtFPS) that exhibits a preferred biosynthesis for geranylgeranyl diphosphate (GGPP) rather than FPP (Tarshis et al., 1996; Fernandez et al., 2000), those yeast lines demonstrated a dramatic accumulation of abietadiene at the expense of farnesol accumulation (FIG. 7). Use of the mtFPS was preferred to other native GGPP synthases because the avian enzyme is particular active as a homodimeric protein and because the enzyme protein is itself relatively small.

Referring to FIG. 6, GC chromatographs of extracts were prepared from yeast engineered for expression of the abietadiene synthase (ABS) gene (upper panel) versus control yeast (those engineered with an empty plasmid DNA, no ABS gene) (lower panel). The yeast lines were grown for approximately 5 days, aliquots of the culture were extracted into hexane, and the hexane extracts then profiled by GC-MS. Cedrene was added to cultures prior to extraction as an external standard to account for sample extraction efficiency (peak 1); farnesol (peak 3) was monitored as an estimation of how much carbon flux to FPP was occurring in the yeast cells; and abietadiene (peak 5) was monitored as a measure of how much isoprenoid intermediates (IPP, DMAPP and FPP) were being diverted to diterpene biosynthesis.

FIG. 7 provides data from GC chromatograms of yeast co-expressing the abietadiene synthase (ABS) and a mutant avian farnesyl diphosphate synthase (mtFPS) (upper panel) versus a yeast line only expressing the ABS gene (lower panel). The yeast lines were grown for approximately 5 days, aliquots of the culture were extracted into hexane, and the hexane extracts then profiled by GC-MS. Cedrene was added to cultures prior to extraction as an external standard to account for sample extraction efficiency (peak 1); farnesol (peak 2) was monitored as an estimation of how much carbon flux to FPP was occurring in the yeast cells, thus escaping channeling to diterpene biosynthesis; and abietadiene (peak 3) was monitored as a measure of how much isoprenoid intermediates (IPP, DMAPP and FPP) were being diverted to specialized diterpene biosynthesis.

Figure 8:
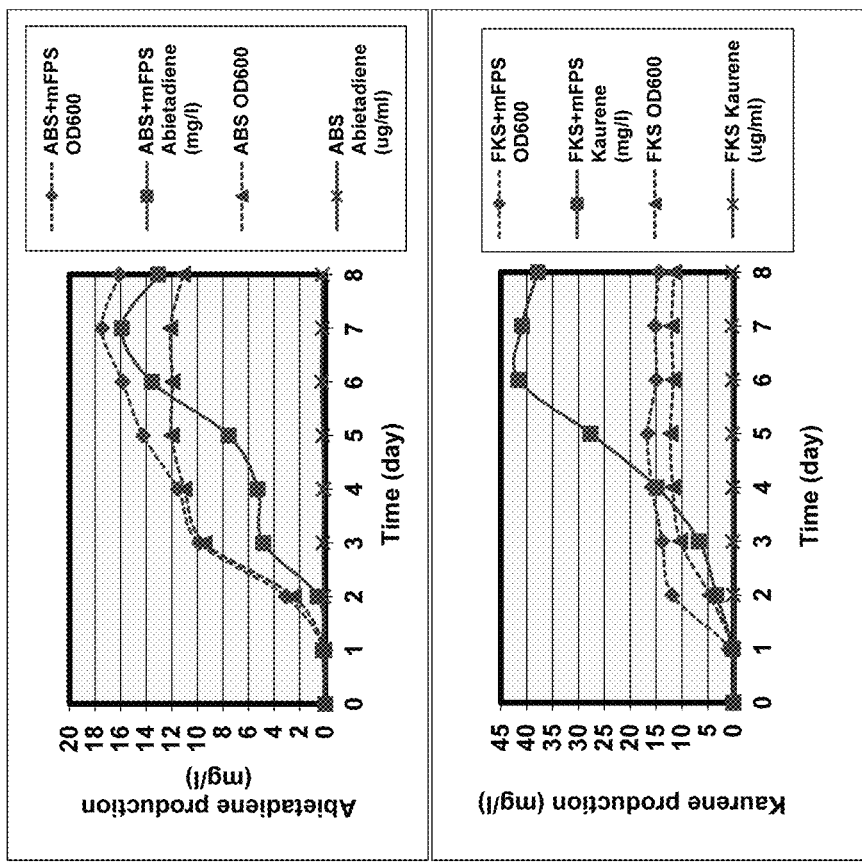
FIG. 8 comprises two graphs showing co-expression of the mFPS gene with different diterpene synthase genes enhances diterpene accumulation.

FIG. 8 comprises graphs for assessing if the co-expression of the mtFPS gene with different diterpene synthases genes enhances diterpene accumulation. In the upper panel of FIG. 8, yeast engineered for expression of the ABS gene or ABS gene plus mtFPS gene were grown under standard conditions and aliquots of the cultures were monitored daily for growth (OD600 nm) and abietadiene accumulation (GC-MS determination). In the lower panel of FIG. 8, yeast were engineered for expression of a second diterpene synthase gene, kaurene synthase, plus and minus co-expression of the mtFPS gene. Cultures were monitored daily for growth (OD600 nm) and kaurene accumulation (GC-MS).

The benefit of co-expressing the mutant FPS gene with other diterpene synthases for the improved yield of diterpene hydrocarbons was examined with other diterpene synthase genes as well. In FIG. 8, co-expression of the mtFPS gene along with a codon optimized fungal kaurene synthase gene (Toyomasu et al., 2000) dramatically improved kaurene accumulation (lower panel) as observed for abietadiene biosynthesis (upper panel). Equally important to note, the enhanced diterpene accumulation due to the co-expression of the mtFPS did not impose any obvious penalty in cell biomass accumulation (OD600 nm). Cell culture growth was, in fact, improved from 20 to 40% when the diterpene synthase genes were co-expressed with the mutant prenyltransferase.

Figure 9:
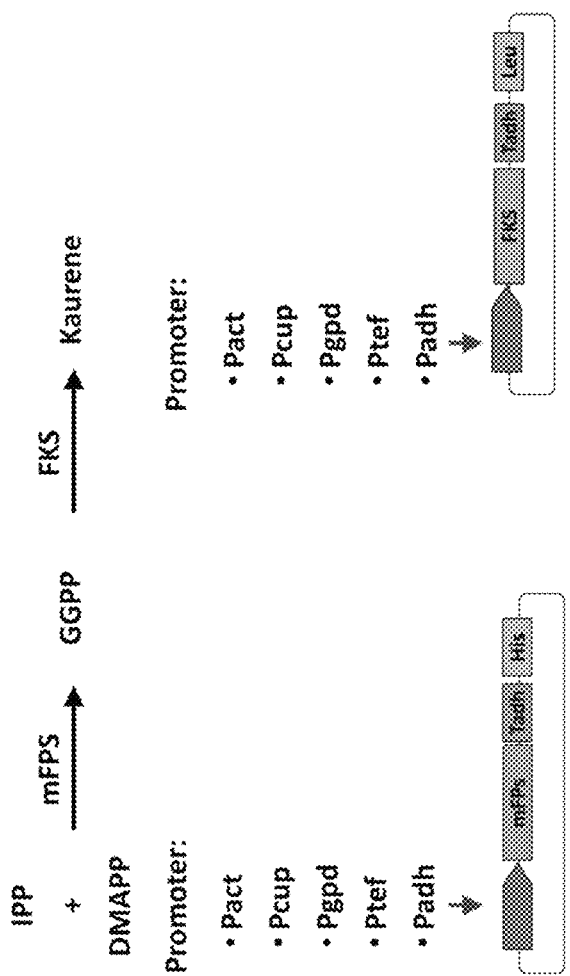
FIG. 9 illustrates a construct design for testing the importance of specific gene promoters for diterpene (kaurene) production in yeast.

II. Identification of Gene Expression Promoters and Vector Configurations to Enhance Diterpene Accumulation The co-expression of the mutant FPS and diterpene synthases provides evidence that the expression level of each gene relative to one another (the stoichiometric relationship) might be an important for optimized diterpene production FIG. 9 is a schematic showing a construct design for testing the importance of specific gene promoters for diterpene (kaurene) production in yeast. A variety of promoter elements were inserted independently upfront of the mtFPS gene and the fungal kaurene synthase gene followed by the yeast being transformed with all possible combinations of each construct. The different transgenic yeast lines would then evaluate for kaurene production levels.

A variety of gene promoter combinations were evaluated for determining the regulation level of target enzymes in the yeast cells as shown in the strategy outline in FIG. 9.

Figure 10:
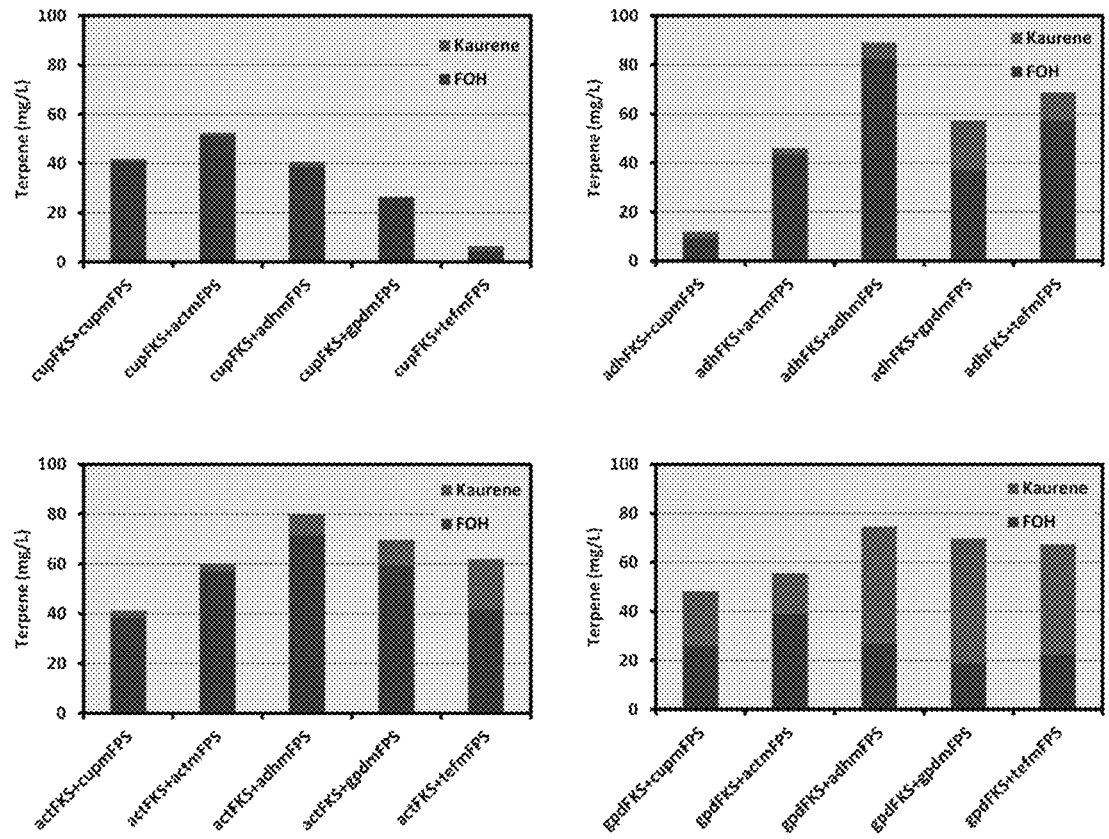
FIG. 10 comprises four graphs showing kaurene and farnesol (FOH) accumulation in yeast engineered for expression of the kaurene synthase and mutant avian FPP synthase driven by different gene promoters.

As shown in FIG. 9, the promoter elements included the actin (act) promoter (Mateus and Avery, 2000), a copper inducible (cup) promoter (Tohoyama et al., 2001), glyceraldehyde phosphate dehydrogenase (gpd) promoter (Bitter and Egan, 1984), transcription elongation factor (tef) promoter (Mumberg et al., 1995), and the alcohol dehydrogenase (adh) promoter, which we previous described using for heterologous expression in yeast (Takahashi et al., 2007). Yeast strain ZX 2-2 was co-transformed with the various two plasmid construct combinations, then individual transformant lines were monitored for kaurene and farnesol accumulation (FIG. 10). While we were obviously screened these lines for the promoter combination giving the highest level of diterpene production, an equal important parameter was the farnesol levels. If a yeast line was efficiently diverting the earlier isoprenoid precursors to diterpene, their farnesol levels would be expected to be equally low. By these criteria, having the GPD promoter direct expression of both the mutant prenyltransferase and the kaurene synthase genes yielded the highest level of kaurene with the greatest efficiency.

The data in the graphs of FIG. 10 were from yeast transformed with the various plasmids noted in FIG. 9, selected for prototrophic growth without leucine or histidine added to the culture media, then grown for 10 days before extracting and chemically profiling aliquots of the cultures by GC-MS. For the line harboring the CUP promoter construct, the cultures were grown for 2 days, then 1 mM copper sulfate was added to the growth media.

Figure 11:
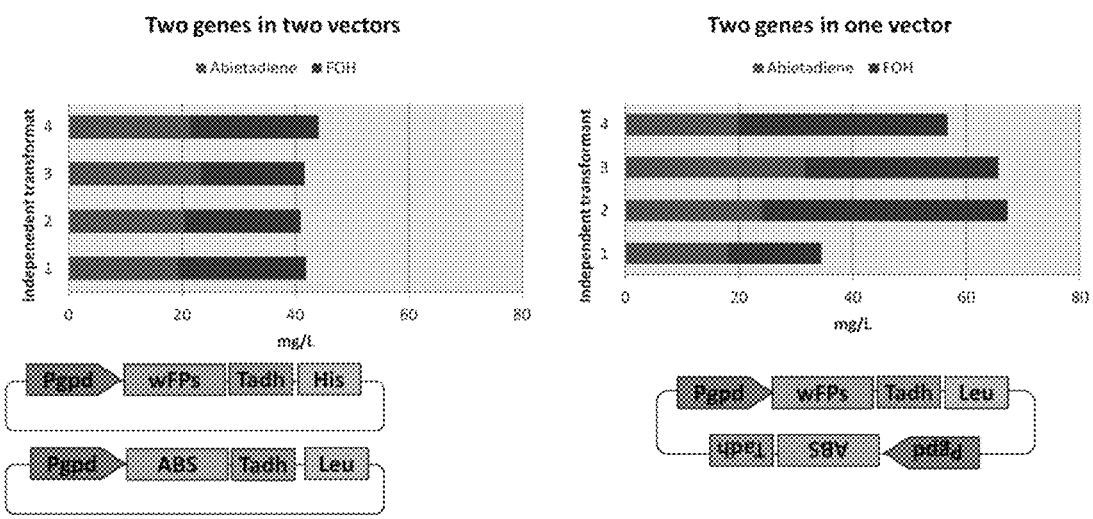
FIG. 11 shows a comparison of vector configuration effects on abietadine production in ZX 2-2 yeast line.

The results of FIG. 10 demonstrated that the absolute level of gene expression and stoichiometry of the encoded enzymes influenced overall diterpene production. Next the prenyltransferase and diterpene synthase genes were assembled in separate plasmid vectors or into a single vector. In this way, we were evaluating whether variation in diterpene accumulation could be associated with possible variation in gene copy number as reflected by possible variation in plasmid copy number, or whether a one-to-one stoichiometry of prenyltransferase and diterpene synthase genes on a single plasmid vector were preferable. In the first examination of these possibilities, the constructs relied on the GPD promoter to drive expression of the prenyltransferase and diterpene synthase genes. The constructs were then introduced into yeast and multiple, independent transformants selected for monitoring diterpene (abietadiene) production and farnesol accumulation (FIG. 11). Farnesol accumulation was monitored as a measure of how much carbon was not efficiently being converted to diterpene. Surprisingly, those transgenic lines with the multiple plasmid constructs exhibited relatively minor variation in the level of diterpene and farnesol accumulated, while the lines transformed with the single vector harboring both the prenyltransferase and diterpene synthase genes showed more than 50% variation in the absolute levels of farnesol and abietadiene. Nonetheless, independent transgenic lines containing the targeted genes on a single plasmid vector also demonstrated greater than 30% more abietadiene and farnesol than when the transgenes were introduced on separate plasmid vectors.

FIG. 11 provides data from test showing how the molecular configuration of the mutant prenyltransferase (mtFPS, geranylgeranyl diphosphate synthase) relative to the diterpene synthase (ABS, abietadiene synthase) might influence diterpene production. The indicated plasmid vectors were transformed into yeast ZX 2-2 and 4 independent transgenic lines grown for 10 days prior to extracting and chemically profiling the extracts by GC-MS for abietadiene and farnesol (FOH) accumulation.

Figure 12:
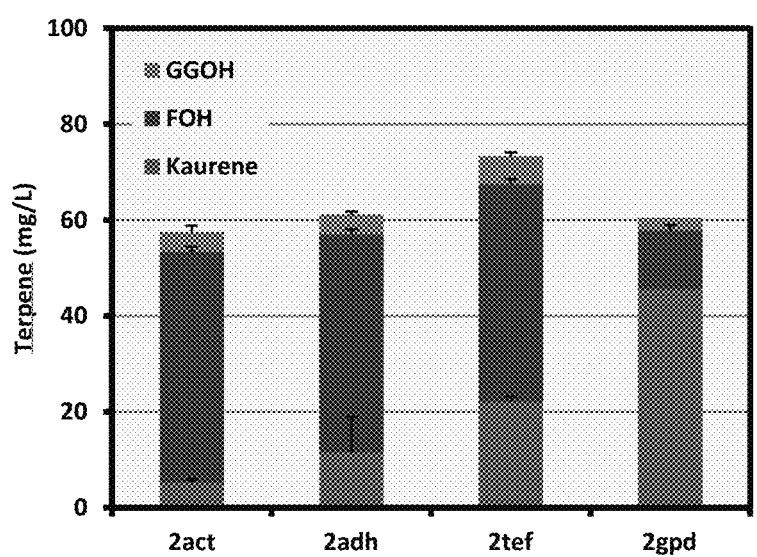
FIG. 12 is a chart showing kaurene, farnesol (FOH) and geranylgeraniol accumulation in yeast engineered for expression of kaurene synthase and mutant avian FPP synthase driven by different gene promoter combinations on a single gene expression vector.

The most optimal vector design suggested by the experimental work up to this point suggest that having both the prenyltransferase and diterpene synthase genes on one plasmid vector and having expression of both genes driven by the GPD promoter was the preferred structural organization. This was confirmed in another experiment where the GPD promoter elements within the single plasmid construct were substituted with the ACT, ADH and TEF promoter elements and the transgenic lines examined for farnesol and kaurene accumulation (FIG. 12). Once again, the combination of the dual combination of the GPD promoters proved superior to any other promoter combination with respect to kaurene yield and efficiency, as noted by the limited about of farnesol accumulating.

The graph of FIG. 12 provides data from evaluating the efficiency of the ACT, ADH, TEF or GPD promoters to direct expression of both the mutant prenyltransferase and kaurene synthase genes on a single plasmid vector for diterpene production. Yeast line ZX 2-2 was transformed with the indicated plasmid vector and a resulting transformant line chemically profiled by GC-MS after 10 days of growth.

III. Optimization of Culture Conditions to Enhance Diterpene Accumulation

Figure 13:
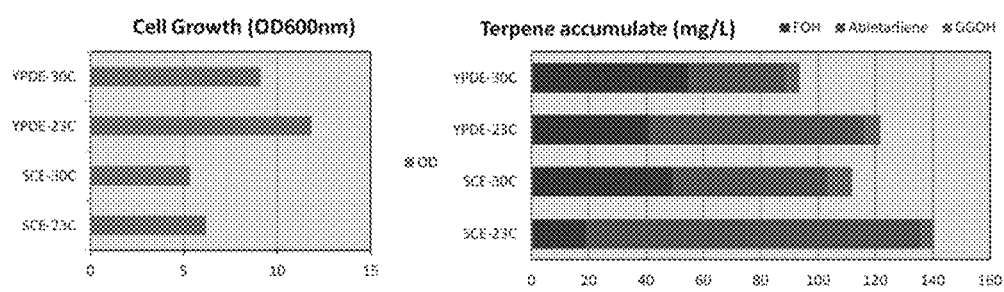
FIG. 13 comprises two charts show culture medium and temperature influences on abietadiene accumulation.

During the evaluation of genes and genetic elements for enhancing diterpene accumulation, variation in diterpene yields with the culture conditions were observed upon examination of these parameters more systematically, it was discovered that for each diterpene target, specific culture conditions could dramatically influence overall diterpene accumulation. In FIG. 13, the accumulation of abietadiene, farnesol and geranylgeraniol by the same yeast line overexpressing the mutant prenyltransferase and abietadiene synthase genes grown under 4 conditions (2 temperatures and 2 media) was examined. Not unexpectedly, when grown in nutrient rich media (YPDE), the yeast grew approximately 2-fold greater than when cultured in selection media (SCE) for 10 days. However, growth of the cultures at 23° C. versus 30° C. had relatively little influence over this 10-day period in terms of overall biomass accumulation. However, a dramatic effect on abietadiene accumulation was noted when the cultures were grown at 23° C. in selection media. Abietadiene accumulation was 2-fold greater under these conditions than when grown at the higher temperature or in the nutrient rich media. The latter observation might be explained by the loss of the recombinant expression plasmid from the yeast grown in the absence of selection pressure provided by the selection media. In contrast, kaurene accumulation by yeast co-expressing the fungal kaurene synthase and mutant prenyltransferase also under the control of GPD promoters was highest in yeast grown in nutrient rich media rather than selection media, even if the cultures were grown for 10 or more days. Cooler culture temperatures appear to improve diterpene accumulation regardless of the diterpene synthase gene used.

FIG. 13 provides data correlating culture media and temperature influence diterpene accumulation. Yeast strain ZX178-08 co-expressing ABS and mtFPS under the direction of the GPD promoter was grown in nutrient rich media (YPDE) or selection media (SCE) at 23° C. or 30° C. for 10 days. Culture growth was then measure at OD600 nm and terpene accumulation was determined by GC-MS.

IV. Decorating Diterpene Hydrocarbon Scaffolds

Figure 14:
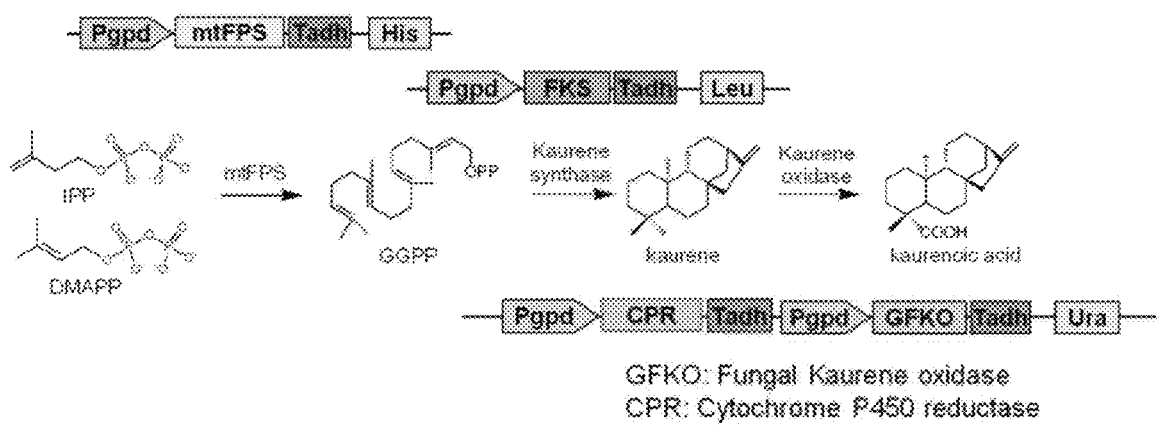
FIG. 14 shows expression constructs designed for producing diterpene acids in yeast in accordance with the present invention.

Having achieved the production of diterpene hydrocarbon production in yeast, more highly modified forms of diterpenes and especially those molecules that might have industrial, agricultural or medicinal applications were sought. For this purpose, we have utilized a 3 plasmid construct design (FIG. 14). Plasmids 1 and 2 are those described above and whose expression in yeast yields robust levels of diterpenes such as kaurene. The third plasmid construct was similarly designed to constructs 1 and 2, but contained a gene encoding for kaurene oxidase, a fungal P450 enzyme (Tudzynski et al., 2001) requiring reducing equivalents from a cytochrome P450 reductase (CPR) (Takahashi et al., 2007) for activity.

These three vector constructs were transformed into yeast line 2-2 and a confirmed transformant evaluated for diterpene production at 23° C. and 30° C. in nutrient rich media and selection media as described before (FIG. 15). The yeast were grown for 10 days before the accumulation of kaurene and its specific oxidation products kaurenal and kaurenoic acid were measured by GC-MS. Consistent with the earlier observations for kaurene production only, maximal production of approximately 200 mg/l of kaurenoic acid was determined for the culture grown in nutrient rich media at the reduced temperature. This diterpene productivity was about 2-fold greater than the next best conditions, which was the same lower temperature with selection growth media.

FIG. 14 is a schematic showing a construct design for producing diterpene acids in yeast in accordance with the present invention. The mutant prenyltransferase (mtFPS) and kaurene synthase (FKS) constructs were described above and the new construct consisting of a gene encoding for a fungal P450 enzyme catalyzing the oxidation of kaurene to it acidic form (kaurene oxidase, GFKO), plus a cytochrome P450 reductase (CPR) that provides reducing equivalents to the kaurene oxidase. Expression of these genes, like the prenyltransferase and kaurene synthase genes, is controlled by the GPD promoter.

Figure 15:
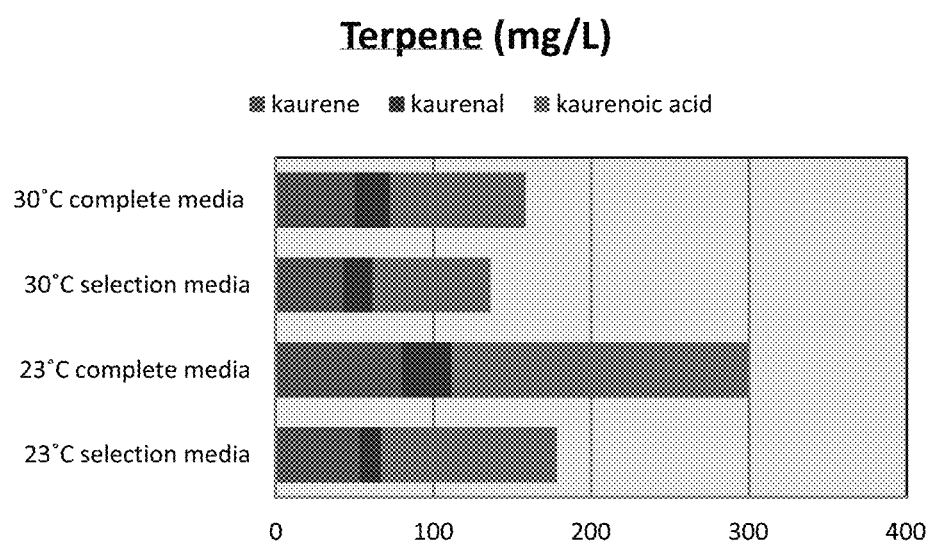
FIG. 15 is a chart showing culture medium and temperature influence kaurenoic acid accumulation in accordance with the present invention.

FIG. 15 shows kaurenoic acid production in yeast is media and temperature sensitive. Yeast strain 2-2 was transformed with the 3 plasmid constructs shown in FIG. 14 and a single confirmed transformant grown under the conditions noted. The diterpene profile was determined after 10 days of growth by GC-MS analysis.

The following experiments, methods and procedures provide additional background with regard to the method for producing diterpene platforms in yeast and the resulting yeast produced. In addition, method for producing various knockout mutations in yeast are described in co-pending U.S. Patent Application Serial No.: 14/092,496, herein incorporated by reference.

The following disclosure provides and demonstrates utility of the yeast lines produced in accordance with the present disclosure for diterpene production via a bioreactor scale-up procedure.

Materials and Methods

Chemical and Media Preparations

All chemical reagents were obtained from Sigma-Aldrich (St. Louis, Mo.), BD Bioscience (Franklin Lakes, N.J.), or Fisher Scientific (Chicago, Ill.), while reagents for molecular manipulations were from Stratagene (San Diego, Calif.), Takara (Shiga, Japan), Invitrogen (San Diego, Calif.), and New England Biolab (Ipswich, Mass.).

Bacteria and yeast were grown using standard culture practices. YPD media for growing yeast without selection consisted of 1% Bactoyeast extract, 2% Bacto-peptone, and 2% glucose (or 0.5% glucose for select experiments). YPDE media was YPD media supplemented with ergosterol (40 mg/L) for ergosterol dependent lines. Minimal media, SCE (pH 5.3), contained 0.67% Bacto-yeast nitrogen base (without amino acids), 2% dextrose, 0.6% succinic acid, 0.14% Sigma yeast dropout solution (-his,-leu,-ura,-trp), uracil (300 mg/L), L-tryptophan (150 mg/L), L-histidine (250 mg/L), L-methionine (200 mg/L), L-leucine (lg/L) and 40 mg/L ergosterol. Cholesterol and ergostrol stocks were 10 mg/mL in 50% Triton X-100, 50% ethanol and kept at −20° C. Selection media was prepared similarly except without supplementing the media with the indicated reagent based on the yeast auxotrophic makers. All solid media plates were prepared with 2% Bacto-Agar.

Yeast Strains

The ZX yeast lines used in these studies were disclosed previously. Essentially, these strains were selected for their ability to utilize exogenous sterol sources under aerobic conditions and were engineered with a knockout mutation in their squalene synthase (ERGS) gene such that the basic mevalonate biosynthetic pathway is operative up to FPP biosynthesis. In some cases, similarly constructed yeast strain CALI7 was utilized (Takahashi et al., 2007).

Yeast Transformation and Culture Performance

Yeast strains were transformed with the respective vector constructs using the FROZEN-EZ Yeast Transformation II Kit (Zymo Research, Orange, Calif.) according to the manufacturer's recommendations. About 1 pg of plasmid DNA was used per transformation, followed by selection on agar plates of SCE medium lacking specified amino acids for the auxotrophic markers (selection media) or YPDE (rich media) at 30° C. Variable numbers of independent colonies were subsequently picked and used to start 3 ml cultures in minimal media to characterize their terpene production capacities. Aliquots of these cultures were analyzed for terpene production after 3-6 days of incubation at 30° C. with shaking by GC-MS. Cultures exhibiting the highest terpene production levels were chosen for further studies and archived as glycerol stocks at −80° C. Selected lines were characterized for cell growth and terpene production using 30 mL shake flask cultures. Starter cultures grown to saturation in minimal media were inoculated into 30 ml SCE or YPDE media and 1 mL aliquots withdrawn at indicated intervals for up to 15 days. Cell growth was monitored as the change in optical density at 600 nm, using appropriate dilutions for cultures at later stages of growth. Terpene production was determined by GC-MS similar to the initial screening method.

GC-MS Detection and Quantification of Terpenes

To determine terpene accumulation levels, aliquots of cultures grown for 3 to 12 days were extracted with hexane and aliquots evaluated by GC-MS. In general, to 1 volume of culture, 1 volume of acetone was added and mixed vigorously for 3 to 5 min to lyse the cells. The sample was then allowed to incubate at room temperature for 10 min before adding 1 volume of hexane containing a known amount of cedrene external standard. The mixture was again mixed vigorously, then centrifuged in a clinical centrifuge for 5 min at maximum speed. The upper organic layer was collected and when necessary, concentrated under a N2 stream to $\frac{1}{10}$ the original volume. An aliquot of the organic phase (1 pl) was then analyzed by GC-MS with a Varian CP-3800 GC coupled to a Varian Saturn 2200 MS/MS (Varian Medical Systems) using a Supelco SLB-5 ms fused silica capillary column (30 m×0.25 mm×0.25 pm film thickness, Supelco). The initial oven temperature was set at 70° C. for 1 min, ramped to 200° C. at 8° C./min, and then ramped to 300° C. at 20° C./min and held for 5 min more. Farnesol and diterpene levels were calculated relative to the cedrene external standard.

Expression Vector Construction

The yeast GPD promoter (Pgpd) was amplified from the PYM-N14 plasmid described by Janke et al. (Janke et al., 2004) using the primers GPD-BamHIF and GPD-NotIR primers and inserted into the pESC-His vector digested with BamH1 and Notl to replace the original GAL1/10 promoters. The resulting plasmid was named pESC-His-gpd. The other promoter elements were obtained similarly.

It will be understood that various details of the presently disclosed subject matter can be changed without departing from the scope of the subject matter disclosed herein. Furthermore, the foregoing description is for the purpose of illustration only, and not for the purpose of limitation.

REFERENCES

Numerous references have been cited throughout this disclosure including the following. All are incorporated by reference.

1. Anderson M, Che P, Song J, Nikolau B, Wurtele E, 1998. 3-Methylcrotonyl-coenzyme A carboxylase is a component of the mitochondrial leucine catabolic pathway in plants. Plant physiology 118, 1127-38.
2. Anterola A, Shanle E, Perroud P-F, Quatrano R (2009) Production of taxa-4(5),11(12)-diene by transgenic *Physcomitrella patens*. Transgenic Research 18: 655-660
3. Asadollahi M A, Maury J, Schalk M, Clark A, Nielsen J, 2010. Enhancement of Farnesyl Diphosphate Pool as Direct Precursor of Sesquiterpenes Through Metabolic Engineering of the Mevalonate Pathway in *Saccharomyces cerevisiae*. Biotechnology and bioengineering 106, 86-96.
4. Barkovich R, Liao J C, 2001. Metabolic engineering of isoprenoids. Metabolic engineering 3, 27-39.
5. Bhilwade H N, Tatewaki N, Nishida H, Konishi T, 2010. Squalene as Novel Food Factor. Current Pharmaceutical Biotechnology 11, 875-80.
6. Bitter G A, Egan K M (1984) Expression Of Heterologous Genes In *Saccharomyces-Cerevisiae* From Vectors Utilizing The Glyceraldehyde-3-Phosphate Dehydrogenase Gene Promoter. Gene 32: 263-274
7. Bourot S, Karst F (1995) ISOLATION AND CHARACTERIZATION OF THE *SACCHAROMYCES-CEREVISIAE* SUT1 GENE INVOLVED IN STEROL UPTAKE. Gene 165: 97-102
8. Bouvier F, Rahier A, Camara B, 2005. Biogenesis, molecular regulation and function of plant isoprenoids. Progress in lipid research 44, 357-429.
9. Buchanan B, Gruissem W, Jones R, 2002. Biochemistry & Molecular Biology of Plants. John Wiley & Sons.
10. Burke Y D, Stark M J, Roach S L, Sen S E, Crowell P L, 1997. Inhibition of pancreatic cancer growth by the dietary isoprenoids farnesol and geraniol. Lipids 32, 151-6.
11. Cardenas C, Quesada A R, Medina M A (2011) Anti-Angiogenic and Anti-Inflammatory Properties of Kahweol, a Coffee Diterpene. Plos One 6
12. Carrau F M, Medina K, Boido E, et al., 2005. De novo synthesis of monoterpenes by *Saccharomyces cerevisiae* wine yeasts. FEMS microbiology letters 243, 107-15.
13. Casida J E (2009) Pest Toxicology: The Primary Mechanisms of Pesticide Action. Chemical Research in Toxicology 22: 609-619
14. DeJong J M, Liu Y L, Bollon A P, Long R M, Jennewein S, Williams D, Croteau R B (2006) Genetic engineering of Taxol biosynthetic genes in *Saccharomyces cerevisiae*. Biotechnology and Bioengineering 93: 212-224
15. Engels B, Dahm P, Jennewein S (2008) Metabolic engineering of taxadiene biosynthesis in yeast as a first step towards Taxol (Paclitaxel) production. Metabolic Engineering 10: 201-206
16. Farhi M, Marhevka E, Masci T, et al., 2011. Harnessing yeast subcellular compartments for the production of plant terpenoids. Metabolic engineering 13, 474-81.
17. Fernandez S M S, Kellogg B A, Poulter C D (2000) Farnesyl diphosphate synthase. Altering the catalytic site to select for geranyl diphosphate activity. Biochemistry 39: 15316-15321
18. Fischer M J C, Meyer S, Claudel P, Bergdoll M, Karst F, 2011. Metabolic Engineering of Monoterpene Synthesis in Yeast. Biotechnology and Bioengineering 108, 1883-92.
19. Grassmann J (2005) Terpenoids as plant antioxidants. In G Litwack, ed, Plant Hormones, Vol 72, pp 505-535
20. Havaux M, Dall'Osto L, Cuine S, Giuliano G, Bassi R (2004) The effect of zeaxanthin as the only xanthophyll on the structure and function of the photosynthetic apparatus in *Arabidopsis thaliana*. Journal of Biological Chemistry 279: 13878-13888
21. Hick A J, Luszniak M C, Pickett J A, 1999. Volatile isoprenoids that control insect behaviour and development. Natural Product Reports 16, 39-54.
22. Huang Z-R, Lin Y-K, Fang J-Y, 2009. Biological and Pharmacological Activities of Squalene and Related Compounds: Potential Uses in Cosmetic Dermatology. Molecules 14, 540-54.
23. Janke C, Magiera M M, Rathfelder N, Taxis C, Reber S, Maekawa H, Moreno-Borchart A, Doenges G, Schwob E, Schiebel E, Knop M (2004) A versatile toolbox for PCR-based tagging of yeast genes: new fluorescent proteins, more markers and promoter substitution cassettes. Yeast 21: 947-962
24. Kovacs K, Zhang L, Linforth R S T, Whittaker B, Hayes C J, Fray R G (2007) Redirection of carotenoid metabolism for the efficient production of taxadiene taxa-4(5), 11(12)-diene in transgenic tomato fruit. Transgenic Research 16: 121-126
25. Maertens J A (2004) History of the development of azole derivatives. Clinical Microbiology and Infection 10: 1-10
26. Maimone T J, Baran P S, 2007. Modern synthetic efforts toward biologically active terpenes. Nature chemical biology 3, 396-407.

27. Martin V J J, Pitera D J, Withers S T, Newman J D, Keasling J D, 2003. Engineering a mevalonate pathway in *Escherichia coli* for production of terpenoids. Nature Biotechnology 21, 796-802.
28. Mateus C, Avery S V (2000) Destabilized green fluorescent protein for monitoring dynamic changes in yeast gene expression with flow cytometry. Yeast 16: 1313-1323
29. Maury J, Asadollahi M A, Møller K, Clark A, Nielsen J, 2005. Microbial isoprenoid production: an example of green chemistry through metabolic engineering. Advances in biochemical engineering/biotechnology 100, 19-51.
30. Mumberg D, Muller R, Funk M (1995) Yeast Vectors For The Controlled Expression Of Heterologous Proteins In Different Genetic Backgrounds. Gene 156: 119-122
31. Nicolaou K C, Yang Z, Liu J J, Ueno H, Nantermet P G, Guy R K, Claiborne C F, Renaud J, Couladouros E A, Paulvannan K, Sorensen E J (1994) TOTAL SYNTHESIS OF TAXOL. Nature 367: 630-634
32. Ohnuma S I, Narita K, Nakazawa T, et al., 1996. A role of the amino acid residue located on the fifth position before the first aspartate-rich motif of farnesyl diphosphate synthase on determination of the final product. The Journal of biological chemistry 271, 30748-54.
33. Porto T S, Rangel R, Furtado N, de Carvalho T C, Martins C H G, Veneziani R C S, Da Costa F B, Vinholis A H C, Cunha W R, Heleno V C G, Ambrosio S R (2009) Pimarane-type Diterpenes: Antimicrobial Activity against Oral Pathogens. Molecules 14: 191-199 Roberts S C (2007) Production and engineering of terpenoids in plant cell culture. Nature Chemical Biology 3: 387-395
34. Reddy L H, Couvreur P, 2009. Squalene: A natural triterpene for use in disease management and therapy. Advanced Drug Delivery Reviews 61, 1412-26.
35. Shianna K V, Dotson W D, Tope S, Parks L W (2001) Identification of a UPC2 homolog in *Saccharomyces cerevisiae* and its involvement in aerobic sterol uptake. Journal of Bacteriology 183: 830-834
36. Takahashi 5, Yeo Y, Greenhagen B T, McMullin T, Song L, Maurina-Brunker J, Rosson R, Noel J P, Chappell J (2007) Metabolic engineering of sesquiterpene metabolism in yeast. Biotechnology and Bioengineering 97: 170-181
37. Tarshis L C, Proteau P J, Kellogg B A, Sacchettini J C, Poulter C D (1996) Regulation of product chain length by isoprenyl diphosphate synthases. Proceedings of the National Academy of Sciences of the United States of America 93: 15018-15023
38. Tohoyama H, Kadota H, Shiraishi E, Inouhe M, Joho M (2001) Induction for the expression of yeast metallothionein gene, CUP1, by cobalt. Microbios 104: 99-104
39. Toyomasu T, Kawaide H, lshizaki A, Shinoda S, Otsuka M, Mitsuhashi W, Sassa T (2000) Cloning of a full-length cDNA encoding ent-kaurene synthase from *Gibberella fujikuroi*: Functional analysis of a bifunctional diterpene cyclase. Bioscience Biotechnology and Biochemistry 64: 660-664
40. Tu Y, 2011. The discovery of artemisinin (qinghaosu) and gifts from Chinese medicine. Nature Medicine 17, 1217-20.
41. Tudzynski B, Hedden P, Carrera E, Gaskin P (2001) The P450-4 gene of *Gibberella fujikuroi* encodes ent-kaurene oxidase in the gibberellin biosynthesis pathway. Applied and Environmental Microbiology 67: 3514-3522
42. Vogel B S, Wildung M R, Vogel G, Croteau R (1996) Abietadiene synthase from grand fir (*Abies grandis*)—cDNA isolation, characterization, and bacterial expression of a bifunctional diterpene cyclase involved in resin acid biosynthesis. Journal of Biological Chemistry 271: 23262-23268
43. Wall M E, Wani M C (1995) PACLITAXEL—FROM DISCOVERY TO CLINIC. In GICTTOIVDM Georg, ed, Taxane Anticancer Agents: Basic Science and Current Status, Vol 583, pp 18-30
44. Wu S Q, Schalk M, Clark A, Miles R B, Coates R, Chappell J (2006) Redirection of cytosolic or plastidic isoprenoid precursors elevates terpene production in plants. Nature Biotechnology 24: 1441-1447
45. Yamaguchi S (2008) Gibberellin metabolism and its regulation. In Annual Review of Plant Biology, Vol 59, pp 225-251
46. Zhang D L, Jennings S M, Robinson G W, Poulter C D (1993) YEAST SQUALENE SYNTHASE—EXPRESSION, PURIFICATION, AND CHARACTERIZATION OF SOLUBLE RECOMBINANT ENZYME. Archives of Biochemistry and Biophysics 304: 133-143
47. Zhou Y J, Gao W, Rong Q, et al., 2012. Modular pathway engineering of diterpenoid synthases and the mevalonic acid pathway for miltiradiene production. Journal of the American Chemical Society 134, 3234-41.

The invention claimed is:

1. A genetically modified yeast for the enhanced expression of terpenes produced by a method comprising:

combining yeast with a chemical mutagenesis agent to induce mutations in the yeast to generate chemically mutated yeast;

selecting chemically mutated yeast which grows in the presence of nystatin, squalestatin and cholesterol, followed by selecting for sterol dependent growth in the presence of squalestatin;

subjecting the sterol dependent growth yeast to an erg9 knockout mutation, to thereby produce sterol dependent growth/erg9 knockout mutation yeast cell lines; and inserting an expression vector into the sterol dependent growth/erg9 knockout mutation yeast cells wherein the expression vector expresses a gene for mutant avian farnesyl diphosphate synthase, to thereby produce the genetically modified yeast having a dispensable sterol biosynthetic pathway and genetically modified with a non-naturally occurring prenyltransferase to thereby alter prenyl diphosphate levels and genetically modified to express a terpene synthase directed to diterpene production.

2. The genetically modified yeast of claim 1, wherein the yeast both has an erg9 knockout and has sterol uptake enhancement (SUE) and the yeast can grow in the presence of squalestatin and nystatin and are dependent on exogenous sterol for growth.

3. The genetically modified yeast of claim 1, wherein the yeast is selected from the group consisting of Candida albicans and Saccharomyces cerevisiae.

4. A method for generating terpene producing yeast cell lines, the method comprising:

combining yeast with a chemical mutagenesis agent to induce mutations in the yeast to generate chemically mutated yeast;

selecting chemically mutated yeast which grows in the presence of nystatin, squalestatin and cholesterol, followed by selecting for sterol dependent growth in the presence of squalestatin;

subjecting the sterol dependent growth yeast to an erg9 knockout mutation, to thereby produce sterol dependent growth/erg9 knockout mutation yeast cell lines; and inserting an expression vector into the sterol dependent growth/erg9 knockout mutation yeast cells wherein the expression vector expresses a gene for mutant avian farnesyl diphosphate synthase.

5. The method of claim 4, wherein subjecting the sterol dependent growth yeast to an erg9 knockout mutation comprises inserting a foreign gene sequence into the sterol dependent growth yeast at the location of erg9 to effect gene replacement, thereby generating the erg9 knockout mutation.

6. The method of claim 5, wherein the foreign gene sequence confers chemical resistance to a selected chemical thereby allowing the sterol dependent growth/erg9 knockout mutation yeast to grow in the presence of the chemical.

7. The method of claim 4, wherein the yeast is selected from the group consisting of *Candida albicans* and *Saccharomyces cerevisiae*.

8. The genetically modified yeast of claim 1, wherein the terpene synthase is kaurene synthase.

9. The genetically modified yeast of claim 1, wherein the prenyltransferase and the terpene synthase are targeted to the cytoplasm of the genetically modified yeast.

10. The generally modified yeast of claim 1, wherein the dispensable sterol biosynthetic pathway comprises a functional mevalonate pathway not coupled to sterol metabolism.

11. The genetically modified yeast of claim 1, wherein the non-naturally occurring prenyltransferase catalyzes the conversion of dimethylallyl pyrophosphate (DMAPP) and isopentenyl diphosphate (IPP) to yield GGPP.

12. The genetically modified yeast of claim 11, wherein the terpene synthase, expressed for diterpene production by genetic modification, is a heterologous diterpene synthase that converts available geranylgeranyl diphosphate (GGPP) to the production of diterpenes.

13. The genetically modified yeast of claim 1, wherein the terpene synthase, expressed for diterpene production by genetic modification, is a heterologous diterpene synthase that converts available geranylgeranyl diphosphate (GGPP) to the production of diterpenes.

14. The genetically modified yeast of claim 1, wherein subjecting the sterol dependent growth yeast to an erg9 knockout mutation comprises inserting a foreign gene sequence into the sterol dependent growth yeast at the location of erg9 to effect gene replacement, thereby generating the erg9 knockout mutation.

15. The genetically modified yeast of claim 14, wherein the foreign gene sequence confers chemical resistance to a selected chemical thereby allowing the sterol dependent growth/erg9 knockout mutation yeast to grow in the presence of the chemical.

16. The genetically modified yeast of claim 1, wherein the sterol is ergosterol.

* * * * *

SEQUENCE LISTING

<160> NUMBER OF SEQ ID NOS: 24

<210> SEQ ID NO 1
<211> LENGTH: 1137
<212> TYPE: DNA
<213> ORGANISM: Gallus gallus

<400> SEQUENCE: 1

```
atgcagcccc atcatcatca taaagagggg cgtatgcata aatttactgg tgtcaatgcc      60
aagtttcagc aacccgcgtt gaggaacctc agcccgtgg tggttgagag ggagagggag      120
gagttcgtgg ggttcttccc gcagatcgtc cgcgatctga ccgaggacgg catcggacac      180
ccggaggtgg gcgacgctgt ggcgcggctg aaggaggtgc tgcaatacaa cgctcccggt      240
gggaaatgca atcgtgggct gacggtggtg gctgcgtacc gggagctgtc ggggccgggg      300
cagaaggatg ctgagagcct gcggtgcgcg ctggccgtgg gttggtgcat cgagttgttc      360
```

```
caggccttct tcctggtggc tgatgatatc atggatcagt ccctcacgcg ccgggggcag    420
ctgtgttggt ataagaagga ggggtcggt ttggatgcca tcaacgactc cttcctcctc    480
gagtcctctg tgtacagagt gctgaagaag tactgcaggc agcggccgta ttacgtgcat    540
ctgttggagc tcttcctgca gaccgcctac cagactgagc tcgggcagat gctggacctc    600
atcacagctc ccgtctccaa agtggatttg agtcacttca gcgaggagag gtacaaagcc    660
atcgttaagt acaagactgc cttctactcc ttctacctac ccgtggctgc tgccatgtat    720
atggttggga tcgacagtaa ggaagaacac gagaatgcca aagccatcct gctggagatg    780
ggggaatact tccagatcca ggatgattac ctggactgct tggggacccc ggcgctcacg    840
gggaaggtgg gcaccgacat ccaggacaat aaatgcagct ggctcgtggt gcagtgcctg    900
cagcgcgtca cgccggagca gcggcagctc ctggaggaca actacggccg taaggagccc    960
gagaaggtgg cgaaggtgaa ggagctgtat gaggccgtgg ggatgagggc tgcgttccag   1020
cagtacgagg agagcagcta ccggcgcctg caggaactga tagagaagca ctcgaaccgc   1080
ctcccgaagg agatcttcct cggcctggca cagaagatct acaaacgcca gaaatga     1137
```

<210> SEQ ID NO 2
<211> LENGTH: 378
<212> TYPE: PRT
<213> ORGANISM: Artificial Sequence
<220> FEATURE:
<223> OTHER INFORMATION: deduced sequence from cDNA from Gallus gallus

<400> SEQUENCE: 2

```
Met Gln Pro His His His His Lys Glu Gly Arg Met His Lys Phe Thr
1               5                  10                  15

Gly Val Asn Ala Lys Phe Gln Gln Pro Ala Leu Arg Asn Leu Ser Pro
            20                  25                  30

Val Val Glu Arg Glu Arg Glu Phe Val Gly Phe Pro Gln
        35                  40                  45

Ile Val Arg Asp Leu Thr Glu Asp Gly Ile Gly His Pro Glu Val Gly
    50                  55                  60

Asp Ala Val Ala Arg Leu Lys Glu Val Leu Gln Tyr Asn Ala Pro Gly
65                  70                  75                  80

Gly Lys Cys Asn Arg Gly Leu Thr Val Val Ala Ala Tyr Arg Glu Leu
                85                  90                  95

Ser Gly Pro Gly Gln Lys Asp Ala Glu Ser Leu Arg Cys Ala Leu Ala
            100                 105                 110

Val Gly Trp Cys Ile Glu Leu Phe Gln Ala Phe Phe Leu Val Ala Asp
        115                 120                 125

Asp Ile Met Asp Gln Ser Leu Thr Arg Arg Gly Gln Leu Cys Trp Tyr
    130                 135                 140

Lys Lys Glu Gly Val Gly Leu Asp Ala Ile Asn Asp Ser Phe Leu Leu
145                 150                 155                 160

Glu Ser Ser Val Tyr Arg Val Leu Lys Lys Tyr Cys Arg Gln Arg Pro
                165                 170                 175

Tyr Tyr Val His Leu Leu Glu Leu Phe Leu Gln Thr Ala Tyr Gln Thr
            180                 185                 190

Glu Leu Gly Gln Met Leu Asp Leu Ile Thr Ala Pro Val Ser Lys Val
        195                 200                 205

Asp Leu Ser His Phe Ser Glu Glu Arg Tyr Lys Ala Ile Val Lys Tyr
    210                 215                 220
```

```
Lys Thr Ala Phe Tyr Ser Phe Tyr Leu Pro Val Ala Ala Met Tyr
225                 230                 235                 240

Met Val Gly Ile Asp Ser Lys Glu Glu His Glu Asn Ala Lys Ala Ile
            245                 250                 255

Leu Leu Glu Met Gly Glu Tyr Phe Gln Ile Gln Asp Asp Tyr Leu Asp
        260                 265                 270

Cys Phe Gly Asp Pro Ala Leu Thr Gly Lys Val Gly Thr Asp Ile Gln
    275                 280                 285

Asp Asn Lys Cys Ser Trp Leu Val Val Gln Cys Leu Gln Arg Val Thr
290                 295                 300

Pro Glu Gln Arg Gln Leu Leu Glu Asp Asn Tyr Gly Arg Lys Glu Pro
305                 310                 315                 320

Glu Lys Val Ala Lys Val Lys Glu Leu Tyr Glu Ala Val Gly Met Arg
            325                 330                 335

Ala Ala Phe Gln Gln Tyr Glu Glu Ser Ser Tyr Arg Arg Leu Gln Glu
        340                 345                 350

Leu Ile Glu Lys His Ser Asn Arg Leu Pro Lys Glu Ile Phe Leu Gly
    355                 360                 365

Leu Ala Gln Lys Ile Tyr Lys Arg Gln Lys
370                 375
```

<210> SEQ ID NO 3
<211> LENGTH: 1155
<212> TYPE: DNA
<213> ORGANISM: Artificial Sequence
<220> FEATURE:
<223> OTHER INFORMATION: engineered sequence

<400> SEQUENCE: 3

```
atgcaccacc atcatcatat gcagccccat catcatcata agagggggcg tatgcataaa      60
tttactggtg tcaatgccaa gtttcagcaa cccgcgttga ggaacctcag ccccgtggtg     120
gttgagaggg agaggagga gttcgtgggg ttcttcccgc agatcgtccg cgatctgacc      180
gaggacggca tcggacaccc ggaggtgggc gacgctgtgg cgcggctgaa ggaggtgctg     240
caatacaacg ctcccggtgg gaaatgcaat cgtgggctga cggtggtggc tgcgtaccgg     300
gagctgtcgg ggccggggca aaggatgct gagagcctgc ggtgcgcgct ggccgtgggt      360
tggtgcatcg agctcttcca ggccgccttc ctggtggctg atgatatcat ggatcagtcc     420
ctcacgcgcc gggggcagct gtgttggtat aagaaggagg gggtcggttt ggatgccatc     480
aacgactcct cctcctcga gtcctctgtg tacagagtgc tgaagaagta ctgcaggcag     540
cggccgtatt acgtgcatct gttggagctc ttcctgcaga ccgcctacca gactgagctc     600
gggcagatgc tggacctcat cacagctccc gtctccaaag tggatttgag tcacttcagc     660
gaggagaggt acaaagccat cgttaagtac aagactgcct tctactcctt ctacctaccc     720
gtggctgctg ccatgtatat ggttgggatc gacagtaagg aagaacacga gaatgccaaa     780
gccatcctgc tggagatggg ggaatacttc agatccagg atgattaccct ggactgcttt     840
ggggacccgg cgctcacggg gaaggtgggc accgacatcc aggacaataa atgcagctgg     900
ctcgtggtgc agtgcctgca gcgcgtcacg ccggagcagc ggcagctcct ggaggacaac     960
tacggccgta aggagcccga aggtggcg aaggtgaagg agctgtatga ggccgtgggg     1020
atgagggctg cgttccagca gtacgaggag agcagctacc ggcgcctgca ggaactgata    1080
gagaagcact cgaaccgcct cccgaaggag atcttcctcg gcctggcaca gaagatctac    1140
aaacgccaga aatga                                                    1155
```

```
<210> SEQ ID NO 4
<211> LENGTH: 34
<212> TYPE: DNA
<213> ORGANISM: Artificial Sequence
<220> FEATURE:
<223> OTHER INFORMATION: primer sequence

<400> SEQUENCE: 4
gtgcatcgag ctcttccagg ccgccttcct ggtg                              34

<210> SEQ ID NO 5
<211> LENGTH: 34
<212> TYPE: DNA
<213> ORGANISM: Artificial Sequence
<220> FEATURE:
<223> OTHER INFORMATION: primer sequence

<400> SEQUENCE: 5
caccaggaag gcggcctgga agagctcgat gcac                              34

<210> SEQ ID NO 6
<211> LENGTH: 385
<212> TYPE: PRT
<213> ORGANISM: Artificial Sequence
<220> FEATURE:
<223> OTHER INFORMATION: deduced sequence

<400> SEQUENCE: 6

Met His His His His His His Met Gln Pro His His His His Lys Glu
1               5                   10                  15

Gly Arg Met His Lys Phe Thr Gly Val Asn Ala Lys Phe Gln Gln Pro
            20                  25                  30

Ala Leu Arg Asn Leu Ser Pro Val Val Glu Arg Glu Arg Glu Glu
        35                  40                  45

Phe Val Gly Phe Phe Pro Gln Ile Val Arg Asp Leu Thr Glu Asp Gly
    50                  55                  60

Ile Gly His Pro Glu Val Gly Asp Ala Val Ala Arg Leu Lys Glu Val
65                  70                  75                  80

Leu Gln Tyr Asn Ala Pro Gly Gly Lys Cys Asn Arg Gly Leu Thr Val
                85                  90                  95

Val Ala Ala Tyr Arg Glu Leu Ser Gly Pro Gly Gln Lys Asp Ala Glu
            100                 105                 110

Ser Leu Arg Cys Ala Leu Ala Val Gly Trp Cys Ile Glu Leu Phe Gln
        115                 120                 125

Ala Ala Phe Leu Val Ala Asp Asp Ile Met Asp Gln Ser Leu Thr Arg
    130                 135                 140

Arg Gly Gln Leu Cys Trp Tyr Lys Lys Glu Gly Val Gly Leu Asp Ala
145                 150                 155                 160

Ile Asn Asp Ser Phe Leu Leu Glu Ser Ser Val Tyr Arg Val Leu Lys
                165                 170                 175

Lys Tyr Cys Arg Gln Arg Pro Tyr Tyr Val His Leu Leu Glu Leu Phe
            180                 185                 190

Leu Gln Thr Ala Tyr Gln Thr Glu Leu Gly Gln Met Leu Asp Leu Ile
        195                 200                 205

Thr Ala Pro Val Ser Lys Val Asp Leu Ser His Phe Ser Glu Glu Arg
    210                 215                 220

Tyr Lys Ala Ile Val Lys Tyr Lys Thr Ala Phe Tyr Ser Phe Tyr Leu
225                 230                 235                 240
```

```
Pro Val Ala Ala Ala Met Tyr Met Val Gly Ile Asp Ser Lys Glu Glu
                245                 250                 255

His Glu Asn Ala Lys Ala Ile Leu Leu Glu Met Gly Glu Tyr Phe Gln
            260                 265                 270

Ile Gln Asp Asp Tyr Leu Asp Cys Phe Gly Asp Pro Ala Leu Thr Gly
        275                 280                 285

Lys Val Gly Thr Asp Ile Gln Asp Asn Lys Cys Ser Trp Leu Val Val
    290                 295                 300

Gln Cys Leu Gln Arg Val Thr Pro Glu Gln Arg Gln Leu Leu Glu Asp
305                 310                 315                 320

Asn Tyr Gly Arg Lys Glu Pro Glu Lys Val Ala Lys Val Lys Glu Leu
                325                 330                 335

Tyr Glu Ala Val Gly Met Arg Ala Ala Phe Gln Gln Tyr Glu Glu Ser
            340                 345                 350

Ser Tyr Arg Arg Leu Gln Glu Leu Ile Glu Lys His Ser Asn Arg Leu
        355                 360                 365

Pro Lys Glu Ile Phe Leu Gly Leu Ala Gln Lys Ile Tyr Lys Arg Gln
    370                 375                 380

Lys
385

<210> SEQ ID NO 7
<211> LENGTH: 2859
<212> TYPE: DNA
<213> ORGANISM: Gibberella fujikuroi

<400> SEQUENCE: 7
atgcctggca aaatcgagaa cggcaccccc aaagacctca agacaggaaa tgactttgta      60
tcagcagcaa agtcgctgct ggaccgcgcc ttcaagagcc atcatagcta ctatggtcta     120
tgttccacca gctgtcaggt atatgacact gcttgggtgg ccatgatacc caagacgaga     180
gacaatgtca agcaatggct gtttcctgag tgcttccact atcttctgaa gactcaggcc     240
gctgatggta gttggggtag tctccccacg acccagactg ctggtattct agacactgct     300
tcagctgtgc ttgcactctt atgtcacgca caagagcctc tgcagatact ggacgtctcg     360
ccagacgaga tgggtctcag gatcgagcac ggggtaactt ctttgaagcg acagctagct     420
gtttggaacg atgttgaaga taccaatcac attggtgtcg agtttattat ccagctttta     480
cttttccatg cttgagaaaga gctcgacgtg ccatcttttg agtttccttg cagaagtatc     540
ttggagagga tgcacggaga gaagctcggc catttcgatt tggagcaagt atatggcaag     600
ccgtcttcac tacttcactc ccttgaagcc tttcttggaa agcttgactt tgatcgcctt     660
tctcaccatc tttatcatgg ctctatgatg gcttcacctt cttccactgc agcctacctc     720
attggtgcaa ccaagtggga cgacgaggct gaagattacc tgaggcacgt tatgagaaat     780
ggtgctggtc acgggaatgg tggcatctca ggcacctttc ctacaacaca ttttgagtgt     840
agctggatca tagcgacact cctgaaggtt ggcttcactt tgaaacaaat cgatggtgat     900
ggcttgcgcg gcttgtcaac tatacttctc gaagcgttga gggacgagaa tggagtaatt     960
ggctttgcac cccgtactgc tgatgttgat gacactgcaa aagctcttct ggcattgagc    1020
cttgtcaatc aacctgtcag cccagatatc atgatcaagg tctttgaagg aaaagatcac    1080
ttcaccacgt tcggatctga acgtgatccc agcttgactt ccaacctcca tgtgctgctg    1140
agtctcctga agcagtccaa tctatcgcaa taccacccac aaatcctgaa gaccacgttg    1200
```

```
ttcacttgcc gatggtggtg gggcagcgac cattgcgtca agataaatg gaatttgagt    1260
catctatacc caaccatgct tctggtggaa gctttcaccg aggtacttca tctcattgat    1320
ggtggcgagc tttctagtct cttttgacgag agcttcaagt gcaagatcgg cctgtcaatc    1380
ttccaggctg tactacgtat catcctcacc caagataacg acggatcttg agaggatat     1440
cgcgagcaaa catgctacgc cattctagct cttgtacagg cacgccatgt atgtttcttc    1500
actcacatgg tggacaggct acagagttgc gtcgaccgtg gcttttcgtg gctcaagtcc    1560
tgcagctttc attctcagga cctcacttgg acgtcaaaga cagcatatga ggttgggttt    1620
gttgctgaag cgtacaagct agcagcccct cagtcagcaa gcctagaggt gcccgccgct    1680
actattggcc acagcgtcac ctcggcggtt ccatcatcgg acttggagaa gtacatgagg    1740
cttgtgcgca agactgcttt gttctcgcca ctggacgagt ggggactcat ggcgtcaatc    1800
attgagtcct cgttcttcgt gcccttcta caagctcagc gcgttgagat ttatccgagg     1860
gacaacatca aggtcgacga ggacaaatac ctgagcatca ttccttttac ttgggtcgga    1920
tgcaacaaca gatcccgcac atttgcatct aacagatggc tctacgatat gatgtacctg    1980
tccctcctgg gctaccagac cgatgagtac atggaagctg tcgctgggcc ggtattcggt    2040
gatgtctctc tgcttcacca gaccatcgac aaggtcatag acaacacaat gggaaactta    2100
gccagggcca atggtaccgt gcacagtggc aatggtcatc agcatgagtc acccaacatt    2160
ggacaagttg aggatactct cactcgcttc accaacagcg tgctcaacca caagatgtt    2220
ctgaattcaa gctcttctga ccaagacact cttcgccgag aattcagaac gttcatgcat    2280
gcccatatca cacagataga ggacaacagt cgcttctcca gcaggcctc cagcgacgct    2340
ttctcttccc cagaacaatc gtacttccaa tgggtcaaca gtacaggagg cagtcacgtc    2400
gcctgcgcgt actcattcgc tttctccaac tgcctaatgt cagcgaatct gctccaaggc    2460
aaggacgcat ttccctccgg cactcagaaa tatctcattt catccgttat gcgtcacgct    2520
acaaatatgt gtcgtatgta caacgacttt gggtccatag ctcgcgataa cgctgagcgg    2580
aatgtgaact cgatccactt ccccgagttc acgttatgta acggaacgtc acagaatctc    2640
gatgaaagga aagagagact ttaaagata gctacgtatg agcaaggtta tcttgatcgt     2700
gctctcgaag ctctggaacg acagtctcgt gatgatgcag gtgatcgtgc tgggtctaag    2760
gatatgagga agctcaagat tgtaaaactg ttctgtgatg tcaccgactt gtatgatcag    2820
ctttacgtga tcaaggacct ttcaagcagc atgaagtga                          2859

<210> SEQ ID NO 8
<211> LENGTH: 952
<212> TYPE: PRT
<213> ORGANISM: Gibberella fujikuroi

<400> SEQUENCE: 8

Met Pro Gly Lys Ile Glu Asn Gly Thr Pro Lys Asp Leu Lys Thr Gly
1               5                   10                  15

Asn Asp Phe Val Ser Ala Ala Lys Ser Leu Leu Asp Arg Ala Phe Lys
            20                  25                  30

Ser His His Ser Tyr Tyr Gly Leu Cys Ser Thr Ser Cys Gln Val Tyr
        35                  40                  45

Asp Thr Ala Trp Val Ala Met Ile Pro Lys Thr Arg Asp Asn Val Lys
    50                  55                  60

Gln Trp Leu Phe Pro Glu Cys Phe His Tyr Leu Leu Lys Thr Gln Ala
65                  70                  75                  80
```

```
Ala Asp Gly Ser Trp Gly Ser Leu Pro Thr Thr Gln Thr Ala Gly Ile
             85                  90                  95

Leu Asp Thr Ala Ser Ala Val Leu Ala Leu Leu Cys His Ala Gln Glu
        100                 105                 110

Pro Leu Gln Ile Leu Asp Val Ser Pro Asp Glu Met Gly Leu Arg Ile
        115                 120                 125

Glu His Gly Val Thr Ser Leu Lys Arg Gln Leu Ala Val Trp Asn Asp
        130                 135                 140

Val Glu Asp Thr Asn His Ile Gly Val Glu Phe Ile Ile Pro Ala Leu
145                 150                 155                 160

Leu Ser Met Leu Glu Lys Glu Leu Asp Val Pro Ser Phe Glu Phe Pro
                165                 170                 175

Cys Arg Ser Ile Leu Glu Arg Met His Gly Glu Lys Leu Gly His Phe
        180                 185                 190

Asp Leu Glu Gln Val Tyr Gly Lys Pro Ser Ser Leu Leu His Ser Leu
        195                 200                 205

Glu Ala Phe Leu Gly Lys Leu Asp Phe Asp Arg Leu Ser His His Leu
        210                 215                 220

Tyr His Gly Ser Met Met Ala Ser Pro Ser Ser Thr Ala Ala Tyr Leu
225                 230                 235                 240

Ile Gly Ala Thr Lys Trp Asp Asp Glu Ala Glu Asp Tyr Leu Arg His
                245                 250                 255

Val Met Arg Asn Gly Ala Gly His Gly Asn Gly Gly Ile Ser Gly Thr
                260                 265                 270

Phe Pro Thr Thr His Phe Glu Cys Ser Trp Ile Ile Ala Thr Leu Leu
                275                 280                 285

Lys Val Gly Phe Thr Leu Lys Gln Ile Asp Gly Asp Gly Leu Arg Gly
        290                 295                 300

Leu Ser Thr Ile Leu Leu Glu Ala Leu Arg Asp Glu Asn Gly Val Ile
305                 310                 315                 320

Gly Phe Ala Pro Arg Thr Ala Asp Val Asp Thr Ala Lys Ala Leu
                325                 330                 335

Leu Ala Leu Ser Leu Val Asn Gln Pro Val Ser Pro Asp Ile Met Ile
                340                 345                 350

Lys Val Phe Glu Gly Lys Asp His Phe Thr Thr Phe Gly Ser Glu Arg
                355                 360                 365

Asp Pro Ser Leu Thr Ser Asn Leu His Val Leu Leu Ser Leu Leu Lys
        370                 375                 380

Gln Ser Asn Leu Ser Gln Tyr His Pro Gln Ile Leu Lys Thr Thr Leu
385                 390                 395                 400

Phe Thr Cys Arg Trp Trp Trp Gly Ser Asp His Cys Val Lys Asp Lys
                405                 410                 415

Trp Asn Leu Ser His Leu Tyr Pro Thr Met Leu Leu Val Glu Ala Phe
                420                 425                 430

Thr Glu Val Leu His Leu Ile Asp Gly Gly Glu Leu Ser Ser Leu Phe
                435                 440                 445

Asp Glu Ser Phe Lys Cys Lys Ile Gly Leu Ser Ile Phe Gln Ala Val
        450                 455                 460

Leu Arg Ile Ile Leu Thr Gln Asp Asn Asp Gly Ser Trp Arg Gly Tyr
465                 470                 475                 480

Arg Glu Gln Thr Cys Tyr Ala Ile Leu Ala Leu Val Gln Ala Arg His
                485                 490                 495

Val Cys Phe Phe Thr His Met Val Asp Arg Leu Gln Ser Cys Val Asp
```

-continued

```
                500                 505                 510
Arg Gly Phe Ser Trp Leu Lys Ser Cys Ser Phe His Ser Gln Asp Leu
            515                 520                 525

Thr Trp Thr Ser Lys Thr Ala Tyr Glu Val Gly Phe Val Ala Glu Ala
            530                 535                 540

Tyr Lys Leu Ala Ala Leu Gln Ser Ala Ser Leu Glu Val Pro Ala Ala
545                 550                 555                 560

Thr Ile Gly His Ser Val Thr Ser Ala Val Pro Ser Ser Asp Leu Glu
                        565                 570                 575

Lys Tyr Met Arg Leu Val Arg Lys Thr Ala Leu Phe Ser Pro Leu Asp
                580                 585                 590

Glu Trp Gly Leu Met Ala Ser Ile Ile Glu Ser Ser Phe Phe Val Pro
            595                 600                 605

Leu Leu Gln Ala Gln Arg Val Glu Ile Tyr Pro Arg Asp Asn Ile Lys
            610                 615                 620

Val Asp Glu Asp Lys Tyr Leu Ser Ile Ile Pro Phe Thr Trp Val Gly
625                 630                 635                 640

Cys Asn Asn Arg Ser Arg Thr Phe Ala Ser Asn Arg Trp Leu Tyr Asp
                        645                 650                 655

Met Met Tyr Leu Ser Leu Leu Gly Tyr Gln Thr Asp Glu Tyr Met Glu
                660                 665                 670

Ala Val Ala Gly Pro Val Phe Gly Asp Val Ser Leu Leu His Gln Thr
            675                 680                 685

Ile Asp Lys Val Ile Asp Asn Thr Met Gly Asn Leu Ala Arg Ala Asn
            690                 695                 700

Gly Thr Val His Ser Gly Asn Gly His Gln His Glu Ser Pro Asn Ile
705                 710                 715                 720

Gly Gln Val Glu Asp Thr Leu Thr Arg Phe Thr Asn Ser Val Leu Asn
                        725                 730                 735

His Lys Asp Val Leu Asn Ser Ser Ser Ser Asp Gln Asp Thr Leu Arg
                740                 745                 750

Arg Glu Phe Arg Thr Phe Met His Ala His Ile Thr Gln Ile Glu Asp
            755                 760                 765

Asn Ser Arg Phe Ser Lys Gln Ala Ser Ser Asp Ala Phe Ser Ser Pro
            770                 775                 780

Glu Gln Ser Tyr Phe Gln Trp Val Asn Ser Thr Gly Gly Ser His Val
785                 790                 795                 800

Ala Cys Ala Tyr Ser Phe Ala Phe Ser Asn Cys Leu Met Ser Ala Asn
                        805                 810                 815

Leu Leu Gln Gly Lys Asp Ala Phe Pro Ser Gly Thr Gln Lys Tyr Leu
                820                 825                 830

Ile Ser Ser Val Met Arg His Ala Thr Asn Met Cys Arg Met Tyr Asn
            835                 840                 845

Asp Phe Gly Ser Ile Ala Arg Asp Asn Ala Glu Arg Asn Val Asn Ser
            850                 855                 860

Ile His Phe Pro Glu Phe Thr Leu Cys Asn Gly Thr Ser Gln Asn Leu
865                 870                 875                 880

Asp Glu Arg Lys Glu Arg Leu Leu Lys Ile Ala Thr Tyr Glu Gln Gly
                        885                 890                 895

Tyr Leu Asp Arg Ala Leu Glu Ala Leu Glu Arg Gln Ser Arg Asp Asp
                900                 905                 910

Ala Gly Asp Arg Ala Gly Ser Lys Asp Met Arg Lys Leu Lys Ile Val
            915                 920                 925
```

Lys Leu Phe Cys Asp Val Thr Asp Leu Tyr Asp Gln Leu Tyr Val Ile
        930                 935                 940

Lys Asp Leu Ser Ser Ser Met Lys
945                 950

<210> SEQ ID NO 9
<211> LENGTH: 2868
<212> TYPE: DNA
<213> ORGANISM: Artificial Sequence
<220> FEATURE:
<223> OTHER INFORMATION: engineered sequence

<400> SEQUENCE: 9

| | | |
|---|---|---|
| atggcggccg caccaggtaa aattgaaaat ggtactccaa agatttgaa aactggtaat | 60 |
| gatttcgttt ctgctgctaa atctttgttg gatagagctt ttaaatctca tcattcttac | 120 |
| tacggtttgt gttctacttc ttgtcaagtt tacgatactg cttgggttgc tatgattcca | 180 |
| aagactagag ataacgttaa gcaatggttg ttcccagaat gtttccatta tttgttgaaa | 240 |
| actcaagctg ctgatggttc ttggggttct ttgccaacta ctcaaactgc tggtattttg | 300 |
| gatactgctt ctgctgtttt ggctttgttg tgtcatgctc aagaaccatt gcaaattttg | 360 |
| gatgtttctc cagatgaaat gggtttgaga attgaacatg gtgttacttc tttgaaaaga | 420 |
| caattggctg tttggaatga tgttgaagat actaatcata ttggtgttga gttcatcatt | 480 |
| ccagctttgt tgtctatgtt ggaaaaagaa ttggatgttc atcttttga atttccatgt | 540 |
| agatctattt tggaaagaat gcatggtgaa aaattgggtc attttgattt ggaacaagtt | 600 |
| tatggtaaac atcttctttt gttgcattct ttggaagcat tccttggtaa attggatttt | 660 |
| gatagattgt ctcatcattt gatcatggt tctatgatgg cttctccatc ttctactgct | 720 |
| gcttatttga ttggtgctac taatgggat gatgaagctg aagattattt gagacatgtt | 780 |
| atgagaaatg gtgctggtca tggtaatggt ggtatttctg gtactttcc aactactcat | 840 |
| ttcgaatgtt cttggatcat cgctactttg ttgaaggttg gttttacttt gaagcaaatt | 900 |
| gatggagatg gtttgagagg tttgtctact attttgttgg aagctcttag agatgaaaat | 960 |
| ggtgttattg gttttgctcc aagaactgct gatgttgatg atactgctaa ggcttttgttg | 1020 |
| gctttgtctt tggttaacca accagtttct ccagatatca tgatcaaggt tttcgagggt | 1080 |
| aaagatcatt tcactacttt cggttctgaa agagatccat ctttgacttc taatttgcat | 1140 |
| gttttgttgt ctttgttgaa gcaatctaat ttgtctcaat accatccaca aatcttgaag | 1200 |
| actactttgt ttacttgtag atggtggtgg ggttctgatc attgtgttaa ggataagtgg | 1260 |
| aatttgtctc atttgtaccc aactatgttg ttggttgaag cattcactga agttttgcat | 1320 |
| tgatcgatg gtggtgaatt gtcttctttg ttcgatgaat cttttaaatg caagatcggt | 1380 |
| ttgtctatct tccaagctgt tttgagaatc atcttgactc aagataacga tggttcttgg | 1440 |
| agaggttata gagaacaaac ttgttatgct attttggctt tggttcaagc tagacatgtt | 1500 |
| tgtttcttta ctcatatggt tgatagattg caatcttgtg ttgatagagg tttttcttgg | 1560 |
| ttgaaatctt gttcttttca ttctcaagat ttgacttgga cttctaaaac tgcttatgaa | 1620 |
| gttggttttg ttgctgaagc atacaaattg gctgctttgc aatctgcttc tttggaagtt | 1680 |
| ccagctgcta ctattggtca ttctgttact tctgctgttc atcttctga tttggaaaag | 1740 |
| tacatgagat tggttagaaa gactgctttg ttttctccat tggatgaatg gggtttgatg | 1800 |
| gcttctatta ttgaatcttc attttcgtt ccattgttgc aagctcaaag agttgaaatc | 1860 |

-continued

```
tacccaagag ataacatcaa ggttgatgag gataagtatt tgtctatcat tccattcact   1920
tgggttggtt gtaacaacag atctagaact ttcgcttcta acagatggtt gtacgatatg   1980
atgtatttgt ctttgttggg ttaccaaact gatgaatata tggaagctgt tgctggtcca   2040
gttttcggag atgtttcttt gttgcatcaa actatcgata aagttattga taacactatg   2100
ggtaatttgg ctagagctaa cggtactgtt cattctggta atggtcatca acatgaatct   2160
ccaaacatcg gtcaagttga agatactttg actagattca ctaactctgt tttgaaccat   2220
aaggatgttt tgaactcttc ctcaagtgat caagatactt tgagaagaga gttcagaact   2280
tttatgcatg ctcatatcac tcaaatcgaa gataattcta gattttctaa gcaagctagt   2340
tctgatgctt tttcttctcc agaacaatct tattttcaat gggttaattc tactggtggt   2400
tctcatgttg cttgtgctta ttcttttgct ttttctaatt gtttgatgtc tgctaatttg   2460
ttgcagggta aagatgcttt cccatctggt actcaaaagt atttgatttc ttctgttatg   2520
agacatgcta ctaacatgtg tagaatgtac aacgatttcg gttctatcgc tagagataac   2580
gctgaaagaa acgttaattc tatccatttc ccagagttca ctttgtgtaa cggtacttct   2640
caaaatttgg atgaaagaaa ggaaagattg ttgaagatcg ctacttacga acaaggttat   2700
ttggatagag ctttggaggc acttgaaaga caatctagag atgatgctgg agatagagct   2760
ggttctaagg atatgagaaa attgaagatc gttaaattgt tttgtgatgt tactgatttg   2820
tatgatcaat gtatgttat  taaagatttg tcttcaagta tgaaataa              2868
```

<210> SEQ ID NO 10
<211> LENGTH: 2115
<212> TYPE: DNA
<213> ORGANISM: Artemisia annua

<400> SEQUENCE: 10

```
atgcaatcaa caacttccgt taagttatct cccttcgatc taatgacggc gttacttaac     60
ggcaaggtat ccttcgacac atcaaacaca tccgatacga atattccgtt agccgtgttt    120
atggagaatc gtgagctttt gatgattta  actacttcgg ttgcggttct gatcggatgc    180
gttgtggtgc ttgtgtggag acggtcgtcg tcggcggcga agaaagcggc ggagtcgccg    240
gtgattgttg taccgaagaa agtgacggag gatgaggttg atgatggacg gaagaaagtt    300
actgtgtttt ttggaactca gactggtact gctgaaggtt ttgctaaggc gcttgttgaa    360
gaggctaaag cgcgatatga aaaggcggtg tttaaagtga ttgatttgga tgattatgcc    420
gctgaagatg atgagtatga ggagaagtta aagaaagaat ctcttgcttt tttctttta    480 gctacgtatg gagatggtga gccgacagat aatgctgcta gattctataa atggtttacc    540
gagggtgaag agaaaggtga atggcttgac aagcttcaat acgcagtgtt tggacttggt    600
aacagacagt atgagcattt caacaagatt gctaaggtgg tcgatgaaaa acttgtggaa    660
cagggtgcaa agcgccttgt tcctgttggc atgggagacg atgatcaatg tatcgaagac    720
gacttcactg catggaaaga gttggtgtgg cctgagttgg atcaattact tcgtgatgag    780
gatgatacat ctgttgccac tccatacaca gctgctgttg cagaataccg tgttgtgttc    840
catgataaac cagagacata tgatcaggat caactgacaa atggccatgc tgttcatgat    900
gctcaacatc catgcagatc caatgtcgct gtcaaaaagg agctccattc ccctctatct    960
gaccggtctt gcactcattt ggaatttgat atctctaata ctggattatc gtatgaaact   1020
ggggaccatg ttggagtcta tgttgagaat ctaagtgaag ttgtggacga agctgaaaaa   1080
ttaataggtt taccgccgca cacttatttc tcagtacaca ctgataacga agacgggaca   1140
```

```
ccacttggtg gagcatcttt gccacctcct ttccctccat gcactttaag aaaagcattg   1200
gcttcctatg ctgatgtttt gagctctcct aaaaagtcag ctttgcttgc tttagctgct   1260
catgccactg attctactga agctgataga ctgaaatttc ttgcgtctcc tgctggaaag   1320
gatgaatatg ctcagtggat agttgcaagc cacagaagtc tccttgaggt catggaggcc   1380
ttcccatcag ctaagcctcc gcttggtgtt tttttttgcat ctgttgcccc acgtttgcag   1440
ccgagatact attccatttc ttcttcccca aagtttgcgc caaataggat tcatgtaact   1500
tgtgcattag tgtatgagca acaccgtca ggccgcgttc acaagggagt ctgttcaaca    1560
tggatgaaga atgccgtgcc tatgacagaa agccaggatt gcagttgggc cccaatttat   1620
gttagaacat ccaatttcag acttccttct gatcctaagg tcccagttat catgattggc   1680
ccaggcactg gattggctcc atttagaggt ttccttcagg aaaggttagc tcagaaggaa   1740
gctgggactg agctcggaac agccatttta ttcttcggat gcaggaatcg caaagtggat   1800
ttcatatatg aagacgagct taataatttt gtggagacgg gggctctttc cgagcttgtt   1860
acggccttct ctcgtgaagg tgccactaag gagtacgtgc aacacaagat gactcagaag   1920
gcttcggata tctggaattt tctctctgag ggagcatatt tgtatgtttg cggtgatgcc   1980
aaaggcatgg ccaaagatgt acatcggact ctgcacacaa ttgtgcaaga cagggatct    2040 ctagactcct caaggcgga gctctacgtg aagaatctac aaatggcagg aagatatctc    2100
cgtgatgtat ggtaa                                                    2115
```

<210> SEQ ID NO 11
<211> LENGTH: 704
<212> TYPE: PRT
<213> ORGANISM: Artemisia annua

<400> SEQUENCE: 11

```
Met Gln Ser Thr Thr Ser Val Lys Leu Ser Pro Phe Asp Leu Met Thr
1               5                   10                  15

Ala Leu Leu Asn Gly Lys Val Ser Phe Asp Thr Ser Asn Thr Ser Asp
            20                  25                  30

Thr Asn Ile Pro Leu Ala Val Phe Met Glu Asn Arg Glu Leu Leu Met
        35                  40                  45

Ile Leu Thr Thr Ser Val Ala Val Leu Ile Gly Cys Val Val Val Leu
    50                  55                  60

Val Trp Arg Arg Ser Ser Ser Ala Ala Lys Lys Ala Ala Glu Ser Pro
65                  70                  75                  80

Val Ile Val Val Pro Lys Lys Val Thr Glu Asp Glu Val Asp Asp Gly
                85                  90                  95

Arg Lys Lys Val Thr Val Phe Phe Gly Thr Gln Thr Gly Thr Ala Glu
            100                 105                 110

Gly Phe Ala Lys Ala Leu Val Glu Glu Ala Lys Ala Arg Tyr Glu Lys
        115                 120                 125

Ala Val Phe Lys Val Ile Asp Leu Asp Asp Tyr Ala Ala Glu Asp Asp
    130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Glu Lys Gly Glu Trp Leu Asp Lys Leu
            180                 185                 190
```

```
Gln Tyr Ala Val Phe Gly Leu Gly Asn Arg Gln Tyr Glu His Phe Asn
            195                 200                 205

Lys Ile Ala Lys Val Val Asp Glu Lys Leu Val Glu Gln Gly Ala Lys
    210                 215                 220

Arg Leu Val Pro Val Gly Met Gly Asp Asp Gln Cys Ile Glu Asp
225                 230                 235                 240

Asp Phe Thr Ala Trp Lys Glu Leu Val Trp Pro Glu Leu Asp Gln Leu
                245                 250                 255

Leu Arg Asp Glu Asp Asp Thr Ser Val Ala Thr Pro Tyr Thr Ala Ala
            260                 265                 270

Val Ala Glu Tyr Arg Val Val Phe His Asp Lys Pro Glu Thr Tyr Asp
            275                 280                 285

Gln Asp Gln Leu Thr Asn Gly His Ala Val His Asp Ala Gln His Pro
    290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
                325                 330                 335

Ser Tyr Glu Thr Gly Asp His Val Gly Val Tyr Val Glu Asn Leu Ser
            340                 345                 350

Glu Val Val Asp Glu Ala Glu Lys Leu Ile Gly Leu Pro Pro His Thr
    355                 360                 365

Tyr Phe Ser Val His Thr Asp Asn Glu Asp Gly Thr Pro Leu Gly Gly
            370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
                405                 410                 415

Ala Leu Ala Ala His Ala Thr Asp Ser Thr Glu Ala Asp Arg Leu Lys
            420                 425                 430

Phe Leu Ala Ser Pro Ala Gly Lys Asp Glu Tyr Ala Gln Trp Ile Val
    435                 440                 445

Ala Ser His Arg Ser Leu Leu Glu Val Met Glu Ala Phe Pro Ser Ala
450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Ser Pro Lys Phe Ala Pro Asn Arg
                485                 490                 495

Ile His Val Thr Cys Ala Leu Val Tyr Glu Gln Thr Pro Ser Gly Arg
            500                 505                 510

Val His Lys Gly Val Cys Ser Thr Trp Met Lys Asn Ala Val Pro Met
    515                 520                 525

Thr Glu Ser Gln Asp Cys Ser Trp Ala Pro Ile Tyr Val Arg Thr Ser
530                 535                 540

Asn Phe Arg Leu Pro Ser Asp Pro Lys Val Pro Val Ile Met Ile Gly
545                 550                 555                 560

Pro Gly Thr Gly Leu Ala Pro Phe Arg Gly Phe Leu Gln Glu Arg Leu
                565                 570                 575

Ala Gln Lys Glu Ala Gly Thr Glu Leu Gly Thr Ala Ile Leu Phe Phe
            580                 585                 590

Gly Cys Arg Asn Arg Lys Val Asp Phe Ile Tyr Glu Asp Glu Leu Asn
    595                 600                 605

Asn Phe Val Glu Thr Gly Ala Leu Ser Glu Leu Val Thr Ala Phe Ser
```

|     |     |     |     | 610 |     |     |     | 615 |     |     |     | 620 |     |     |
| --- | --- | --- | --- | --- | --- | --- | --- | --- | --- | --- | --- | --- | --- | --- |
| Arg | Glu | Gly | Ala | Thr | Lys | Glu | Tyr | Val | Gln | His | Lys | Met | Thr | Gln | Lys |
| 625 |     |     |     | 630 |     |     |     | 635 |     |     |     |     |     |     | 640 |

| Ala | Ser | Asp | Ile | Trp | Asn | Phe | Leu | Ser | Glu | Gly | Ala | Tyr | Leu | Tyr | Val |
| --- | --- | --- | --- | --- | --- | --- | --- | --- | --- | --- | --- | --- | --- | --- | --- |
|     |     |     |     | 645 |     |     |     |     |     | 650 |     |     |     | 655 |     |

| Cys | Gly | Asp | Ala | Lys | Gly | Met | Ala | Lys | Asp | Val | His | Arg | Thr | Leu | His |
| --- | --- | --- | --- | --- | --- | --- | --- | --- | --- | --- | --- | --- | --- | --- | --- |
|     |     |     |     | 660 |     |     |     |     |     | 665 |     |     |     | 670 |     |

| Thr | Ile | Val | Gln | Glu | Gln | Gly | Ser | Leu | Asp | Ser | Ser | Lys | Ala | Glu | Leu |
| --- | --- | --- | --- | --- | --- | --- | --- | --- | --- | --- | --- | --- | --- | --- | --- |
|     |     |     | 675 |     |     |     |     | 680 |     |     |     |     | 685 |     |     |

| Tyr | Val | Lys | Asn | Leu | Gln | Met | Ala | Gly | Arg | Tyr | Leu | Arg | Asp | Val | Trp |
| --- | --- | --- | --- | --- | --- | --- | --- | --- | --- | --- | --- | --- | --- | --- | --- |
|     | 690 |     |     |     |     | 695 |     |     |     |     | 700 |     |     |     |     |

<210> SEQ ID NO 12
<211> LENGTH: 1530
<212> TYPE: DNA
<213> ORGANISM: Arabidopsis thaliana

<400> SEQUENCE: 12

| | | |
|---|---|---|
| atggccttct tctccatgat ctccattctc cttggctttg ttatctcctc cttcatcttc | 60 |
| atcttcttct tcaagaaact tctctccttc tccagaaaga acatgtctga agtctccact | 120 |
| ctcccctctg ttccagtggt accagggttt cctgttattg ggaacttgct gcaactaaaa | 180 |
| gagaagaaac tcacaagac tttcactaga tggtcagaga tttatggtcc tatttactct | 240 |
| ataaagatgg gttcttcttc tcttattgtc ctcaattcta ctgagactgc caaagaggcc | 300 |
| atggtgacgc ggttttcgtc tatctcaacg aggaagttgt caaatgcgtt gacagtcctt | 360 |
| acttgtgaca aatctatggt tgctactagt gattatgatg atttccacaa gttggtgaaa | 420 |
| cggtgtctct tgaacggtct tttgggtgct aatgcacaga acgaaaaag acattacaga | 480 |
| gatgcactca ttgaaaatgt gtcttccaag ttgcatgccc atgctaggga ccatccacaa | 540 |
| gaacctgtaa acttcagagc tatatttgag catgagcttt cggtgtagc attgaagcaa | 600 |
| gcttttggga agatgtgga atccatttat gttaaagaac tcggtgtgac tttgtcgaaa | 660 |
| gacgagatct tcaaggtttt agtacatgac atgatggaag gtgcaattga tgttgattgg | 720 |
| agagacttct tcccatactt gaaatggatt ccaaataaaa gttttgaagc aagaatccag | 780 |
| caaaagcata aacgtagact cgcagtgatg aatgctctga ttcaagatcg actgaagcag | 840 |
| aatggttcag aatcggatga tgattgctat ctcaacttct tgatgtcgga agcgaaaaca | 900 |
| ctaaccaagg agcaaattgc tatcttggtt tgggagacga ttatcgagac agctgacact | 960 |
| actttggtta caactgaatg ggccatctat gagctcgcta agcatccaag tgtccaagat | 1020 |
| cgtctgtgca agaaatcca aatgtctgc ggaggagaaa agttcaaaga gagcaattg | 1080 |
| tctcaagttc cttatctcaa tggagtcttt catgaaacgc ttaggaaata cagtcctgct | 1140 |
| cctctagttc ccattcgcta cgcccacgag gatacgcaaa tcggaggcta tcatgtccct | 1200 |
| gcaggaagtg agattgcaat aaacatatat ggatgcaaca tggataagaa gcgttgggag | 1260 |
| agaccagagg actggtggcc ggagcgggtt cttgatgatg gcaaatatga aacgtcagat | 1320 |
| cttcacaaga caatggcgtt tggagcggga aagagggttt gtgctggtgc tcttcaagca | 1380 |
| tctctcatgg caggcattgc tattggaaga ttagtgcaag aattcgagtg gaagcttaga | 1440 |
| gatggcgaag aagagaatgt ggatacatat ggcttgacct ctcagaagct ttatcctctt | 1500 |
| atggctatta tcaatccaag gcgttcttaa | 1530 |

<210> SEQ ID NO 13

<211> LENGTH: 509
<212> TYPE: PRT
<213> ORGANISM: Arabidopsis thaliana

<400> SEQUENCE: 13

```
Met Ala Phe Phe Ser Met Ile Ser Ile Leu Leu Gly Phe Val Ile Ser
 1               5                  10                  15

Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
         35                  40                  45

Gly Phe Pro Val Ile Gly Asn Leu Leu Gln Leu Lys Glu Lys Lys Pro
 50                  55                  60

His Lys Thr Phe Thr Arg Trp Ser Glu Ile Tyr Gly Pro Ile Tyr Ser
 65                  70                  75                  80

Ile Lys Met Gly Ser Ser Leu Ile Val Leu Asn Ser Thr Glu Thr
                 85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
290                 295                 300

Gln Ile Ala Ile Leu Val Trp Glu Thr Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
370                 375                 380

Ile Arg Tyr Ala His Glu Asp Thr Gln Ile Gly Gly Tyr His Val Pro
```

```
               385                 390                 395                 400
Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
                420                 425                 430

Asp Gly Lys Tyr Glu Thr Ser Asp Leu His Lys Thr Met Ala Phe Gly
                435                 440                 445

Ala Gly Lys Arg Val Cys Ala Gly Ala Leu Gln Ala Ser Leu Met Ala
                450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
                500                 505

<210> SEQ ID NO 14
<211> LENGTH: 1578
<212> TYPE: DNA
<213> ORGANISM: Gibberella fujikuroi

<400> SEQUENCE: 14
atgagtaagt ccaacagcat gaacagtacc agccatgaaa cgttattcca gcagctcgtc      60
ttaggtcttg acagaatgcc gctaatggac gttcactggc tgatctacgt ggcctttggc     120
gcttggttat gctcttatgt catccatgtc ctatcgtcct cttctacagt caaagtgccc     180
gtcgtaggct accgcagcgt ctttgagcct acatggcttc tccgtttgcg ctttgtttgg     240 gaaggggggat ctatcatcgg ccaaggctac aacaaattta agactctat cttccaggtg     300 cgaaagcttg gtaccgatat cgtcatcatc ccgccaaact acatcgatga ggtcagaaag     360
ctgtcccaag acaagactcg ctcggtcgag cccttcatca atgactttgc gggacagtat     420
acacggggca tggtctttct gcaaagtgat ttgcagaacc gtgtgattca gcagcggttg     480
acgccaaaac tcgtatcgtt gacaaaggta atgaaggagg agcttgacta tgccttgacc     540
aaagagatgc ctgacatgaa gaatgatgaa tgggttgaag tcgacatttc ttccatcatg     600
gtcaggctca tatcacgcat ctcagccaga gtgtttctcg gtccagagca ctgccgcaac     660
caagaatggt tgacgaccac tgcagagtac agcgagagcc tgttcataac tggctttatt     720
ctccgcgttg tcccccatat tctaagacca ttcatagccc cgctgctacc ctcctacaga     780
acactacttc gcaacgtctc gtcaggtcga agagttattg gagacatcat cgctcccag      840 caaggtgatg gcaacgagga catcctgtca tggatgaggg atgctgcgac aggggaagaa     900
aagcaaattg acaacattgc cagcggatg cttatcctga gtctcgcgtc tattcacact     960
acggcaatga cgatgacgca tgctatgtat gacttatgtg cttgccctga gtacatagag    1020
cctcttagag atgaggtcaa aagtgtcgtt ggcgctagtg gttgggacaa gacggcgttg    1080
aatcgattcc acaaactcga cagctttctc aaagagtcac aacgcttcaa ccccgtgttc    1140
ctcttaacgt tcaatcgcat ttatcaccaa tccatgacac tctcagatgg caccaacatc    1200
ccatcaggca ctcgcatcgc ggttccctct cacgcgatgc ttcaggactc agcgcatgtc    1260
ccaggcccga cgccaccaac cgagtttgat ggatttagat actcaaagat tcgctcagac    1320
tcaaactatg cacagaaaata tctcttctcc atgactgatt ctagtaacat ggcgtttggg    1380
tatgggaaat acgcctgccc agggcggttc tatgcatcta atgagatgaa gctgactttg    1440
```

```
gcgatactcc ttttacaatt tgagttcaag ttgccagatg ggaaaggaag accacgaaat    1500
atcactattg atagtgacat gatacctgat ccgagagcta ggctgtgcgt taggaagcga    1560
tcactgagag atgaatga                                                  1578
```

<210> SEQ ID NO 15
<211> LENGTH: 525
<212> TYPE: PRT
<213> ORGANISM: Gibberella fujikuroi

<400> SEQUENCE: 15

```
Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
        35                  40                  45

His Val Leu Ser Ser Ser Thr Val Lys Val Pro Val Val Gly Tyr
    50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
                85                  90                  95

Ile Phe Gln Val Arg Lys Leu Gly Thr Asp Ile Val Ile Pro Pro
            100                 105                 110

Asn Tyr Ile Asp Glu Val Arg Lys Leu Ser Gln Asp Lys Thr Arg Ser
        115                 120                 125

Val Glu Pro Phe Ile Asn Asp Phe Ala Gly Gln Tyr Thr Arg Gly Met
    130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
                165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
        195                 200                 205

Ala Arg Val Phe Leu Gly Pro Glu His Cys Arg Asn Gln Glu Trp Leu
    210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
            260                 265                 270

Ile Gly Asp Ile Ile Arg Ser Gln Gln Gly Asp Gly Asn Glu Asp Ile
        275                 280                 285

Leu Ser Trp Met Arg Asp Ala Ala Thr Gly Glu Glu Lys Gln Ile Asp
    290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Val Gly Ala
            340                 345                 350
```

Ser Gly Trp Asp Lys Thr Ala Leu Asn Arg Phe His Lys Leu Asp Ser
    355                 360                 365

Phe Leu Lys Glu Ser Gln Arg Phe Asn Pro Val Phe Leu Leu Thr Phe
    370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Pro Thr Glu Phe Asp Gly Phe
            420                 425                 430

Arg Tyr Ser Lys Ile Arg Ser Asp Ser Asn Tyr Ala Gln Lys Tyr Leu
        435                 440                 445

Phe Ser Met Thr Asp Ser Ser Asn Met Ala Phe Gly Tyr Gly Lys Tyr
    450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
            500                 505                 510

Ala Arg Leu Cys Val Arg Lys Arg Ser Leu Arg Asp Glu
        515                 520                 525

<210> SEQ ID NO 16
<211> LENGTH: 1567
<212> TYPE: DNA
<213> ORGANISM: Artificial Sequence
<220> FEATURE:
<223> OTHER INFORMATION: engineered synthetic Codon optimized Gibberella
      fujikuroi Gibberella fujikuroi Kaurene Oxidase (GFKO) gene

<400> SEQUENCE: 16
atgagtaaga gtaacagtat gaacagtaca tcccacgaaa ctttattcca acaattagta      60
ttaggtttag atagaatgcc tttgatggat gtccattggt taatctatgt tgcctttggt     120
gcttggttat gttcttacgt aatacacgtc ttgtcttcat ccagtacagt taagtacca     180 gttgtaggtt atagatcagt tttcgaacct acctggttgt taagattgag atttgtttgg     240
gaaggtggtt ccatcatcgg tcaaggttac aacaaattca aggatagtat cttccaagtt     300
agaaagttag gtacagacat agtaatcatt ccacctaact acatcgatga agttagaaaa     360
ttgtctcaag acaagactag atcagtagaa ccttttatta cgatttcgc aggtcaatac      420 acaagaggta tggtcttttt gcaatccgac ttacaaaaca gagttattca acaaagattg     480
accccaaaat tggtttcttt aactaaagta atgaaggaag aattggatta cgccttaact     540
aaagaaatgc tgatatgaa gaacgacgaa tgggtcgaag ttgatatttc ttctatcatg      600
gttagattaa tatccagaat cagtgctaga gtcttcttgg gtcctgaaca ttgcagaaat     660
caagaatggt tgactacaac cgcagaatat tccgaaagtt tgtttatcac aggtttcatt     720
ttgagagtcg ttccacatat cttgagacct tttatcgcac cattgttgcc ttcatacaga     780
actttgttga gaaacgtatc cagtggtaga agagtcatcg gtgacattat cagatctcaa     840
caaggtgacg gtaacgaaga catttttatca tggatgagag atgctgcaac aggtgaagaa     900
aagcaaatcg acaacatcgc tcaagaatg ttgatattgt ctttagcttc aatacatact      960
acagcaatga ccatgactca cgccatgtat gatttgtgtg cttgcccaga atacattgaa    1020

```
cctttgagag acgaagttaa atctgtagtc ggtgcatcag gttgggataa gactgccttg      1080
aacagattcc ataaattgga ctccttttta aagaaagtc aaagattcaa tccagttttc       1140
ttgttgacct ttaacagaat ctatcaccaa tccatgactt taagtgatgg tacaaatatc      1200
ccatctggta ctagaattgc agttccttcc catgccatgt tgcaagatag tgcccacgtt      1260
ccaggtccta caccacctac cgaatttgat ggtttcagat actctaagat cagatctgac      1320
tcaaactacg ctcaaaagta cttattctca atgactgatt cttcaaacat ggcttttggt      1380
tatggtaaat acgcatgtcc aggtagattt tacgcctcta acgaaatgaa gttgacattg      1440
gctatcttgt tgttgcaatt cgagtttaaa ttgccagatg gtaaaggtag acctagaaat      1500
attaccatag attctgacat gatacctgac ccaagagcaa gattatgcgt tagaaaaaga      1560
agtttga                                                                1567
```

<210> SEQ ID NO 17
<211> LENGTH: 2607
<212> TYPE: DNA
<213> ORGANISM: Abies grandis

<400> SEQUENCE: 17

```
atggccatgc cttcctcttc attgtcatca cagattccca ctgctgctca tcatctaact        60
gctaacgcac aatccattcc gcatttctcc acgacgctga atgctggaag cagtgctagc       120
aaacggagaa gcttgtacct acgatggggt aaggttcaa acaagatcat tgcctgtgtt        180
ggagaaggtg gtgcaaccctc tgttccttat cagtctgctg aaaagaatga ttcgctttct      240
tcttctacat tggtgaaacg agaatttcct ccaggatttt ggaaggatga tcttatcgat       300
tctctaacgt catctcacaa ggttgcagca tcagacgaga agcgtatcga gacattaata       360
tccgagatta agaatatgtt tagatgtatg ggctatggcg aaacgaatcc ctctgcatat       420
gacactgctt gggtagcaag gattccagca gttgatggct ctgacaaccc tcactttcct      480
gagacggttg aatggattct tcaaaatcag ttgaaagatg ggtcttgggg tgaaggattc      540
tacttcttgg catatgacag aatactggct acacttgcat gtattattac ccttacccctc     600 tggcgtactg gggagacaca agtacagaaa ggtattgaat tcttcaggac acaagctgga      660
aagatggaag atgaagctga tagtcatagg ccaagtggat ttgaaatagt atttcctgca      720
atgctaaagg aagctaaaat cttaggcttg gatctgcctt acgatttgcc attcctgaaa      780
caaatcatcg aaaagcggga ggctaagctt aaaaggattc ccactgatgt tctctatgcc      840
cttccaacaa cgttattgta ttcttttgga ggtttacaag aatagtaga ctggcagaaa       900 ataatgaaac ttcaatccaa ggatggatca tttctcagct ctccggcatc tacagcggct      960
gtattcatgc gtacagggaa caaaaagtgc ttggatttct tgaactttgt cttgaagaaa     1020
ttcggaaacc atgtgccttg tcactatccg cttgatctat ttgaacgttt gtgggcggtt      1080
gatacagttg agcggctagg tatcgatcgt catttcaaag aggagatcaa ggaagcattg      1140
gattatgttt acagccattg ggacgaaaga ggcattggat gggcgagaga gaatcctgtt      1200
cctgatattg atgatacagc catgggcctt cgaatcttga gattacatgg atacaatgta      1260
tcctcagatg ttttaaaaac atttagagat gagaatgggg agttcttttg cttcttgggt      1320
caaacacaga gaggagttac agacatgtta aacgtcaatc gttgttcaca tgtttcattt      1380 ccggagaaa cgatcatgga agaagcaaaa ctctgtaccg aaaggtatct gaggaatgct      1440
ctggaaaatg tggatgcctt tgacaaatgg gcttttaaaa agaatattcg gggagaggta      1500
gagtatgcac tcaaatatcc ctggcataag agtatgccaa ggttggaggc tagaagctat      1560
```

```
attgaaaact atgggccaga tgatgtgtgg cttggaaaaa ctgtatatat gatgccatac   1620
atttcgaatg aaaagtattt agaactagcg aaactggact tcaataaggt gcagtctata   1680
caccaaacag agcttcaaga tcttcgaagg tggtggaaat catccggttt cacggatctg   1740
aatttcactc gtgagcgtgt gacgaaaata tatttctcac cggcatcctt tatctttgag   1800
cccgagtttt ctaagtgcag agaggtttat acaaaaactt ccaatttcac tgttatttta   1860
gatgatcttt atgacgccca tggatcttta gacgatctta gttgttcac agaatcagtc     1920 aaaagatggg atctatcact agtggaccaa atgccacaac aaatgaaaat atgttttgtg   1980
ggtttctaca atacttttaa tgatatagca aagaaggac gtgagaggca agggcgcgat    2040
gtgctaggct acattcaaaa tgtttggaaa gtccaacttg aagcttacac gaaagaagca   2100
gaatggtctg aagctaaata tgtgccatcc ttcaatgaat acatagagaa tgcgagtgtg   2160
tcaatagcat tgggaacagt cgttctcatt agtgctcttt tcactgggga ggttcttaca   2220
gatgaagtac tctccaaaat tgatcgcgaa tctagatttc ttcaactcat gggcttaaca   2280
gggcgtttgg tgaatgacac caaaacttat caggcagaga gaggtcaagg tgaggtggct   2340
tctgccatac aatgttatat gaaggaccat cctaaaatct ctgaagaaga agctctacaa   2400
catgtctata gtgtcatgga aaatgccctc gaagagttga atagggagtt tgtgaataac   2460
aaaataccgg atatttacaa aagactggtt tttgaaactg caagaataat gcaactcttt   2520
tatatgcaag gggatggttt gacactatca catgatatgg aaattaaaga gcatgtcaaa   2580
aattgcctct ccaaccagt tgcctag                                        2607
```

<210> SEQ ID NO 18
<211> LENGTH: 868
<212> TYPE: PRT
<213> ORGANISM: Abies grandis

<400> SEQUENCE: 18

```
Met Ala Met Pro Ser Ser Ser Leu Ser Ser Gln Ile Pro Thr Ala Ala
1               5                   10                  15

His His Leu Thr Ala Asn Ala Gln Ser Ile Pro His Phe Ser Thr Thr
            20                  25                  30

Leu Asn Ala Gly Ser Ser Ala Ser Lys Arg Arg Ser Leu Tyr Leu Arg
        35                  40                  45

Trp Gly Lys Gly Ser Asn Lys Ile Ile Ala Cys Val Gly Glu Gly Gly
    50                  55                  60

Ala Thr Ser Val Pro Tyr Gln Ser Ala Glu Lys Asn Asp Ser Leu Ser
65                  70                  75                  80

Ser Ser Thr Leu Val Lys Arg Glu Phe Pro Pro Gly Phe Trp Lys Asp
                85                  90                  95

Asp Leu Ile Asp Ser Leu Thr Ser Ser His Lys Val Ala Ala Ser Asp
            100                 105                 110

Glu Lys Arg Ile Glu Thr Leu Ile Ser Glu Ile Lys Asn Met Phe Arg
        115                 120                 125

Cys Met Gly Tyr Gly Glu Thr Asn Pro Ser Ala Tyr Asp Thr Ala Trp
    130                 135                 140

Val Ala Arg Ile Pro Ala Val Asp Gly Ser Asp Asn Pro His Phe Pro
145                 150                 155                 160

Glu Thr Val Glu Trp Ile Leu Gln Asn Gln Leu Lys Asp Gly Ser Trp
                165                 170                 175

Gly Glu Gly Phe Tyr Phe Leu Ala Tyr Asp Arg Ile Leu Ala Thr Leu
```

-continued

```
            180                 185                 190
Ala Cys Ile Ile Thr Leu Thr Leu Trp Arg Thr Gly Glu Thr Gln Val
            195                 200                 205
Gln Lys Gly Ile Glu Phe Phe Arg Thr Gln Ala Gly Lys Met Glu Asp
            210                 215                 220
Glu Ala Asp Ser His Arg Pro Ser Gly Phe Glu Ile Val Phe Pro Ala
225                 230                 235                 240
Met Leu Lys Glu Ala Lys Ile Leu Gly Leu Asp Leu Pro Tyr Asp Leu
            245                 250                 255
Pro Phe Leu Lys Gln Ile Ile Glu Lys Arg Glu Ala Lys Leu Lys Arg
            260                 265                 270
Ile Pro Thr Asp Val Leu Tyr Ala Leu Pro Thr Thr Leu Leu Tyr Ser
            275                 280                 285
Leu Glu Gly Leu Gln Glu Ile Val Asp Trp Gln Lys Ile Met Lys Leu
            290                 295                 300
Gln Ser Lys Asp Gly Ser Phe Leu Ser Ser Pro Ala Ser Thr Ala Ala
305                 310                 315                 320
Val Phe Met Arg Thr Gly Asn Lys Lys Cys Leu Asp Phe Leu Asn Phe
            325                 330                 335
Val Leu Lys Lys Phe Gly Asn His Val Pro Cys His Tyr Pro Leu Asp
            340                 345                 350
Leu Phe Glu Arg Leu Trp Ala Val Asp Thr Val Glu Arg Leu Gly Ile
            355                 360                 365
Asp Arg His Phe Lys Glu Glu Ile Lys Glu Ala Leu Asp Tyr Val Tyr
            370                 375                 380
Ser His Trp Asp Glu Arg Gly Ile Gly Trp Ala Arg Glu Asn Pro Val
385                 390                 395                 400
Pro Asp Ile Asp Asp Thr Ala Met Gly Leu Arg Ile Leu Arg Leu His
            405                 410                 415
Gly Tyr Asn Val Ser Ser Asp Val Leu Lys Thr Phe Arg Asp Glu Asn
            420                 425                 430
Gly Glu Phe Phe Cys Phe Leu Gly Gln Thr Gln Arg Gly Val Thr Asp
            435                 440                 445
Met Leu Asn Val Asn Arg Cys Ser His Val Ser Phe Pro Gly Glu Thr
450                 455                 460
Ile Met Glu Glu Ala Lys Leu Cys Thr Glu Arg Tyr Leu Arg Asn Ala
465                 470                 475                 480
Leu Glu Asn Val Asp Ala Phe Asp Lys Trp Ala Phe Lys Lys Asn Ile
            485                 490                 495
Arg Gly Glu Val Glu Tyr Ala Leu Lys Tyr Pro Trp His Lys Ser Met
            500                 505                 510
Pro Arg Leu Glu Ala Arg Ser Tyr Ile Glu Asn Tyr Gly Pro Asp Asp
            515                 520                 525
Val Trp Leu Gly Lys Thr Val Tyr Met Met Pro Tyr Ile Ser Asn Glu
            530                 535                 540
Lys Tyr Leu Glu Leu Ala Lys Leu Asp Phe Asn Lys Val Gln Ser Ile
545                 550                 555                 560
His Gln Thr Glu Leu Gln Asp Leu Arg Arg Trp Trp Lys Ser Ser Gly
            565                 570                 575
Phe Thr Asp Leu Asn Phe Thr Arg Glu Arg Val Thr Glu Ile Tyr Phe
            580                 585                 590
Ser Pro Ala Ser Phe Ile Phe Glu Pro Glu Phe Ser Lys Cys Arg Glu
            595                 600                 605
```

```
Val Tyr Thr Lys Thr Ser Asn Phe Thr Val Ile Leu Asp Asp Leu Tyr
    610                 615                 620

Asp Ala His Gly Ser Leu Asp Leu Lys Leu Phe Thr Glu Ser Val
625                 630                 635                 640

Lys Arg Trp Asp Leu Ser Leu Val Asp Gln Met Pro Gln Gln Met Lys
                645                 650                 655

Ile Cys Phe Val Gly Phe Tyr Asn Thr Phe Asn Asp Ile Ala Lys Glu
                660                 665                 670

Gly Arg Glu Arg Gln Gly Arg Asp Val Leu Gly Tyr Ile Gln Asn Val
                675                 680                 685

Trp Lys Val Gln Leu Glu Ala Tyr Thr Lys Glu Ala Glu Trp Ser Glu
    690                 695                 700

Ala Lys Tyr Val Pro Ser Phe Asn Glu Tyr Ile Glu Asn Ala Ser Val
705                 710                 715                 720

Ser Ile Ala Leu Gly Thr Val Val Leu Ile Ser Ala Leu Phe Thr Gly
                725                 730                 735

Glu Val Leu Thr Asp Glu Val Leu Ser Lys Ile Asp Arg Glu Ser Arg
                740                 745                 750

Phe Leu Gln Leu Met Gly Leu Thr Gly Arg Leu Val Asn Asp Thr Lys
            755                 760                 765

Thr Tyr Gln Ala Glu Arg Gly Gln Gly Glu Val Ala Ser Ala Ile Gln
    770                 775                 780

Cys Tyr Met Lys Asp His Pro Lys Ile Ser Glu Glu Ala Leu Gln
785                 790                 795                 800

His Val Tyr Ser Val Met Glu Asn Ala Leu Glu Leu Asn Arg Glu
                805                 810                 815

Phe Val Asn Asn Lys Ile Pro Asp Ile Tyr Lys Arg Leu Val Phe Glu
                820                 825                 830

Thr Ala Arg Ile Met Gln Leu Phe Tyr Met Gln Gly Asp Gly Leu Thr
    835                 840                 845

Leu Ser His Asp Met Glu Ile Lys Glu His Val Lys Asn Cys Leu Phe
850                 855                 860

Gln Pro Val Ala
865

<210> SEQ ID NO 19
<211> LENGTH: 2607
<212> TYPE: DNA
<213> ORGANISM: Artificial Sequence
<220> FEATURE:
<223> OTHER INFORMATION: engineered sequence

<400> SEQUENCE: 19
atggctatgc ctagttcttc tctcagttca caaattccaa ctgctgctca ccacttaaca      60
gcaaacgcac aaagtattcc acatttttct actacactta atgctggatc tagtgcttct     120
aagaggagat cattgtattt gagatgggga aaaggatcca caagattat tgcatgcgtg      180 ggagaaggag gtgcaacatc agttccttac caatctgctg agaagaatga ttctttaagt     240
tcttcaacac ttgtgaaaag ggagtttcca cctggttttt ggaaagatga tctcattgat     300
tctttaactt cttcccataa agtggctgca tccgatgaaa aaggattga gactctcatt      360 tctgaaatta gaacatgtt tagatgtatg ggttacggag aaactaaccc ttctgcttac     420
gatacagctt gggttgctag gattccagct gtggatggta gtgataaccc acatttttct      480
gagactgttg aatggattct tcagaatcag ctcaaagatg gttcttgggg agaaggattc     540
```

```
tatttcttag cttacgatag aattttggca actttggctt gcattattac tttgacactt      600
tggagaactg gtgaaacaca agttcagaag ggtattgaat ttttcaggac tcaagcagga      660
aagatggagg atgaggctga tagtcacaga ccttcaggtt tcgagattgt gtttccagca      720
atgttgaaag aggctaagat tcttggattg gatcttcctt acgatttgcc atttctcaag      780
caaattattg agaaaagaga agctaagctc aaaaggattc ctacagatgt tctctacgca      840
ttaccaacaa ctcttttgta ttcttttggaa ggacttcaag aaattgttga ttggcaaaag     900
attatgaaac tccaaagtaa ggatggatct tttctctcat ctcctgcttc tactgctgct      960
gtttttatga ggacaggtaa caagaagtgt ttagatttct taaatttcgt gctcaaaaag      1020
tttggaaatc atgttccatg ccactatcct cttgatttat ttgaaagact ttgggctgtt      1080
gatacagtgg agaggcttgg tattgatagg cattttaaag aagaaattaa ggaggcattg      1140
gattatgttt actctcattg ggatgagaga ggaattggat gggctagaga aaaccctgtt      1200
cctgatattg atgatacagc aatgggtctt agaattttaa gattgcatgg atacaatgtt      1260
tcttcagatg ttttaaaaac atttagagat gagaatggag agttcttctg cttttttaggt    1320
cagacacaaa ggggagttac agatatgttg aatgttaaca gatgttctca tgttagtttc      1380
cctggtgaga ctattatgga ggaagctaag ttgtgcacag agagatatct tagaaatgca      1440
ttggagaatg ttgatgcttt cgataaatgg gcattcaaaa agaatattag gggtgaagtg      1500
gaatatgctc tcaagtaccc atggcataag tctatgccta ggttggaggc tagatcatat      1560
attgagaact atggtcctga tgatgtttgg cttggaaaaa cagtgtacat gatgccttat      1620
atttcaaatg aaaaatacct tgaactcgct aagctcgatt ttaataaggt tcagtctatt      1680
caccaaactg agttgcagga tttaaggagg tggtggaaat cttcaggatt cactgatctt      1740
aattttacta gagagagagt tactgagatt tacttctcac ctgctagttt tattttcgaa      1800
ccagagttct caaatgtag agaggtttat acaaaaacta gtaatttcac agttattttg        1860
gatgatttgt acgatgctca cggtagtctc gatgatctta aactttttac agaatcagtt      1920
aaaagatggg atttgtcatt agttgatcaa atgccacaac aaatgaagat tgttttgtg       1980
ggattttaca atacttttaa tgatattgct aaagagggta gggagagaca aggtagagat      2040
gttcttggat atattcagaa cgtttggaaa gtgcagttag aggcttatac aaaagaagca      2100
gagtggtctg aggcaaagta tgtgccatct ttcaatgagt acattgaaaa cgcatctgtg      2160
agtattgctc tcggtactgt tgtgcttatt tcagctttat ttacaggaga ggtgcttact      2220
gatgaagtgt tgtccaaaat tgatagggag agtagattc ttcaacttat gggtcttaca        2280
ggtaggcttg ttaatgatac aaagacttat caagctgaaa ggggtcaagg agaagttgct      2340
tctgctattc aatgttatat gaaggatcat cctaaaattt ctgaagaaga agcattgcaa      2400
catgtttatt cagtgatgga aaacgcactc gaagaattaa atagggagtt cgttaacaac      2460
aaaattccag atatttataa aagacttgtt tttgaaactg ctagaattat gcagctcttt      2520
tacatgcaag gtgatggatt aactttgtcc catgatatgg aaattaagga gcacgttaaa      2580
aattgtttgt tccaacctgt tgcataa                                          2607
```

<210> SEQ ID NO 20
<211> LENGTH: 658
<212> TYPE: DNA
<213> ORGANISM: Artificial Sequence
<220> FEATURE:
<223> OTHER INFORMATION: engineered sequence

<400> SEQUENCE: 20

```
gagctcagtt tatcattatc aatactcgcc atttcaaaga atacgtaaat aattaatagt      60
agtgattttc ctaactttat ttagtcaaaa aattagcctt ttaattctgc tgtaacccgt     120
acatgcccaa aataggggc gggttacaca gaatatataa catcgtaggt gtctgggtga      180
acagtttatt cctggcatcc actaaatata atggagcccg cttttaagc tggcatccag      240
aaaaaaaaag aatcccagca ccaaaatatt gttttcttca ccaaccatca gttcataggt     300
ccattctctt agcgcaacta cagagaacag gggcacaaac aggcaaaaaa cgggcacaac     360
ctcaatggag tgatgcaacc tgcctggagt aaatgatgac acaaggcaat tgacccacgc     420
atgtatctat ctcatttct tacaccttct attaccttct gctctctctg atttggaaaa      480
agctgaaaaa aaaggttgaa accagttccc tgaaattatt ccctacttg actaataagt     540
atataaagac ggtaggtatt gattgtaatt ctgtaaatct atttcttaaa cttcttaaat    600
tctacttta tagttagtct ttttttagt tttaaaacac cagaacttag tttcgacg       658
```

<210> SEQ ID NO 21
<211> LENGTH: 666
<212> TYPE: DNA
<213> ORGANISM: Artificial Sequence
<220> FEATURE:
<223> OTHER INFORMATION: engineered sequence

<400> SEQUENCE: 21

```
ttctggcaac caaacccata tacatcggga ttcctataat accttcgttg gtctccctaa     60
catgtaggtg gcggagggga gatatacaat agaacagata ccagacaaga cataatgggc    120
taaacaagac tacaccaatt acactgcctc attgatggtg gtacataacg aactaatact    180
gtagccctag acttgatagc catcatcata tcgaagtttc actacccttt ttccatttgc    240
catctattga agtaataata ggcgcatgca acttctttc tttttttc ttttctctct       300
ccccccgttgt tgtctcacca tatccgcaat gacaaaaaaa tgatggaaga cactaaagga    360
aaaaattaac gacaaagaca gcaccaacag atgtcgttgt tccagagctg atgaggggta    420
tctcgaagca cacgaaactt ttccttcct tcattcacgc acactactct ctaatgagca    480
acggtatacg gccttccttc cagttacttg aatttgaaat aaaaaaagt ttgctgtctt    540
gctatcaagt ataaatagac ctgcaattat taatctttg tttcctcgtc attgttctcg    600
ttcccttct tccttgtttc tttttctgca caatatttca agctataccca agcatacaat    660
caacta                                                               666
```

<210> SEQ ID NO 22
<211> LENGTH: 408
<212> TYPE: DNA
<213> ORGANISM: Artificial Sequence
<220> FEATURE:
<223> OTHER INFORMATION: engineered sequence

<400> SEQUENCE: 22

```
gagctcatag cttcaaaatg tttctactcc ttttttactc ttccagattt tctcggactc     60
cgcgcatcgc cgtaccactt caaaacaccc aagcacagca tactaaattt ccctctcttc    120
ttcctctagg gtgtcgttaa ttacccgtac taaaggtttg gaaagaaaaa aagagaccgc    180
ctcgtttctt tttcttcgtc gaaaaaggca ataaaaattt ttatcacgtt tcttttctt    240
gaaaatttt ttttgatttt ttttctcttt cgatgacctc ccattgatat ttaagttaat    300
aaacggtctt caatttctca gtttcagtt tcatttttct tgttctatta caacttttt    360
```

```
tacttcttgc tcattagaaa gaaagcatag caatctaatc taagtttt        408
```

<210> SEQ ID NO 23
<211> LENGTH: 481
<212> TYPE: DNA
<213> ORGANISM: Artificial Sequence
<220> FEATURE:
<223> OTHER INFORMATION: engineered sequence

<400> SEQUENCE: 23

```
tagtaagccg atcccattac cgacatttgg gcgctatacg tgcatatgtt catgtatgta    60
tctgtattta aaacactttt gtattatttt tcctcatata tgtgtatagg tttatacgga   120
tgatttaatt attacttcac cacccttat ttcaggctga tatcttagcc ttgttactag   180
ttagaaaaag acatttttgc tgtcagtcac tgtcaagaga ttcttttgct ggcatttctt   240
ctagaagcaa aaagagcgat gcgtcttttc cgctgaaccg ttccagcaaa aaagactacc   300
aacgcaatat ggattgtcag aatcatataa aagagaagca aataactcct tgtcttgtat   360
caattgcatt ataatatctt cttgttagtg caatatcata tagaagtcat cgaaatagat   420
attaagaaaa acaaactgta caatcaatca atcaatcatc acataaatcc ggacgacaga   480
g                                                                  481
```

<210> SEQ ID NO 24
<211> LENGTH: 421
<212> TYPE: DNA
<213> ORGANISM: Artificial Sequence
<220> FEATURE:
<223> OTHER INFORMATION: engineered sequence

<400> SEQUENCE: 24

```
ggatcctcaa aacccttaaa aacatatgcc tcaccctaac atattttcca attaaccctc    60
aatatttctc tgtcacccgg cctctatttt ccattttctt ctttacccgc cacgcgtttt   120
tttctttcaa attttttct tccttcttct tttcttcca cgtcctcttg cataaataaa    180
taaaccgttt tgaaaccaaa ctcgcctctc tctctccttt ttgaaatatt tttgggtttg   240
tttgatcctt tccttcccaa tctctcttgt ttaatatata ttcatttata tcacgctctc   300
tttttatctt cctttttttc ctctctcttg tattcttcct tcccctttct actcaaacca   360
agaagaaaaa gaaaaggtca atctttgtta aagaatagga tcttctacta catcagcttt   420
t                                                                  421
```